US010413251B2

(12) United States Patent
Golda et al.

(10) Patent No.: US 10,413,251 B2
(45) Date of Patent: Sep. 17, 2019

(54) WEARABLE CARDIAC MONITOR

(71) Applicant: RHYTHM DIAGNOSTIC SYSTEMS, INC., San Francisco, CA (US)

(72) Inventors: George Stefan Golda, El Granada, CA (US); Daniel Van Zandt Moyer, Menlo Park, CA (US); Mark P. Marriott, Palo Alto, CA (US); Sam Eletr, Paris (FR); Bruce O'Neil, San Francisco, CA (US)

(73) Assignee: RHYTHM DIAGNOSTIC SYSTEMS, INC., San Francisco, CA (US)

( * ) Notice: Subject to any disclaimer, the term of this patent is extended or adjusted under 35 U.S.C. 154(b) by 0 days.

(21) Appl. No.: 13/837,748

(22) Filed: Mar. 15, 2013

(65) Prior Publication Data

US 2014/0100432 A1 Apr. 10, 2014

Related U.S. Application Data

(60) Provisional application No. 61/710,768, filed on Oct. 7, 2012.

(51) Int. Cl.
*A61B 5/00* (2006.01)
*A61B 5/0205* (2006.01)
(Continued)

(52) U.S. Cl.
CPC .......... *A61B 5/7214* (2013.01); *A61B 5/0002* (2013.01); *A61B 5/0059* (2013.01);
(Continued)

(58) Field of Classification Search
CPC . A61B 5/7214; A61B 5/0059; A61B 5/02416; A61B 5/0205; A61B 5/02125;
(Continued)

(56) References Cited

U.S. PATENT DOCUMENTS 4,141,366 A 2/1979 Cross, Jr. et al.
4,164,215 A * 8/1979 Finlayson .......... A61B 5/04004 600/508

(Continued)

FOREIGN PATENT DOCUMENTS

CN 2785556 Y 6/2006
CN 101822533 A 9/2010

(Continued)

OTHER PUBLICATIONS

International Search Report and Written Opinion of the International Searching Authority. International Application No. PCT/US2013/063748 issued by the United State Patent Office, dated Feb. 27, 2014, 15 pages, Alexandria Virginia.

(Continued)

*Primary Examiner* — Gary Jackson
*Assistant Examiner* — Youwon Kahng
(74) *Attorney, Agent, or Firm* — Peter B. Scull; Hamilton, DeSanctis & Cha LLP

(57) ABSTRACT

Systems, methods and devices for reducing noise in cardiac monitoring including wearable monitoring devices having at least one electrode for cardiac monitoring; in some implementations, the wearable device using a composite adhesive having at least one conductive portion applied adjacent the electrode; and, in some implementations, including circuitry adaptations for the at least one electrode to act as a proxy driven right leg electrode.

7 Claims, 13 Drawing Sheets

(51) Int. Cl.

| | |
|---|---|
| ***A61B 5/026*** | (2006.01) |
| ***A61B 5/0295*** | (2006.01) |
| ***A61B 5/0408*** | (2006.01) |
| ***A61B 5/11*** | (2006.01) |
| ***A61B 5/0432*** | (2006.01) |
| ***A61B 5/0402*** | (2006.01) |
| ***A61B 5/08*** | (2006.01) |
| ***A61B 5/021*** | (2006.01) |
| *A61B 5/1455* | (2006.01) |
| *A61B 5/024* | (2006.01) |
| *A61B 5/0456* | (2006.01) |

(52) U.S. Cl.

CPC .......... *A61B 5/0205* (2013.01); *A61B 5/0261* (2013.01); *A61B 5/0295* (2013.01); *A61B 5/02125* (2013.01); *A61B 5/02141* (2013.01); *A61B 5/0402* (2013.01); *A61B 5/04085* (2013.01); *A61B 5/04087* (2013.01); *A61B 5/04325* (2013.01); *A61B 5/08* (2013.01); *A61B 5/11* (2013.01); *A61B 5/6828* (2013.01); *A61B 5/72* (2013.01); *A61B 5/7207* (2013.01); *A61B 5/0006* (2013.01); *A61B 5/02438* (2013.01); *A61B 5/0456* (2013.01); *A61B 5/1118* (2013.01); *A61B 5/14551* (2013.01); *A61B 5/14552* (2013.01); *A61B 5/6833* (2013.01); *A61B 5/721* (2013.01); *A61B 5/7275* (2013.01); *A61B 2560/0295* (2013.01); *A61B 2560/0412* (2013.01)

(58) Field of Classification Search

CPC . A61B 5/02141; A61B 5/0261; A61B 5/0295; A61B 5/0402; A61B 5/04085; A61B 5/04087; A61B 5/04325; A61B 5/08; A61B 5/11; A61B 5/6828; A61B 5/72; A61B 5/7207

USPC .................................. 600/300–301, 508–528

See application file for complete search history.

(56) References Cited

U.S. PATENT DOCUMENTS 4,221,223 A 9/1980 Linden
4,224,948 A 9/1980 Cramer
4,230,127 A 10/1980 Larson
4,295,472 A 10/1981 Adams
4,360,030 A 11/1982 Citron et al.
4,412,546 A 11/1983 Barthels
4,583,190 A * 4/1986 Salb ...................... A61B 5/048 708/404
4,674,511 A 6/1987 Cartmell
4,803,992 A 2/1989 Lemelson
4,869,254 A 9/1989 Stone et al.
4,880,304 A 11/1989 Jaeb et al.
4,902,886 A 2/1990 Smisko
4,934,372 A 6/1990 Corenman et al.
4,938,228 A 7/1990 Righter et al.
5,184,620 A 2/1993 Cudahy et al.
5,215,087 A 6/1993 Anderson
5,224,486 A 7/1993 Lerman et al.
5,261,401 A 11/1993 Baker et al.
5,265,579 A 11/1993 Ferrari
5,307,818 A * 5/1994 Segalowitz .................. 600/509
5,372,125 A 12/1994 Lyons
5,419,321 A 5/1995 Evans
5,448,991 A 9/1995 Polson
5,465,715 A 11/1995 Lyons
5,465,727 A * 11/1995 Reinhold, Jr. ................ 600/523
5,511,553 A 4/1996 Segalowitz et al.
5,549,116 A 8/1996 Mauer
5,632,272 A 5/1997 Diab et al.
5,673,692 A 10/1997 Schulze et al.
5,730,143 A 3/1998 Schwarzberg
5,817,008 A 10/1998 Rafert et al.
5,931,791 A 8/1999 Saltzstein et al.
5,938,597 A 8/1999 Stratbucker
6,032,060 A * 2/2000 Carim et al. ................. 600/372
6,041,247 A 3/2000 Weckstrom
6,088,607 A 7/2000 Diab et al.
6,122,535 A 9/2000 Kaestle et al.
6,263,222 B1 7/2001 Diab et al.
6,327,487 B1 * 12/2001 Stratbucker ........ A61B 5/04085 600/382
6,385,473 B1 5/2002 Haines et al.
6,453,186 B1 9/2002 Lovejoy et al.
6,525,386 B1 2/2003 Mills
6,569,095 B2 5/2003 Eggers
6,662,033 B2 12/2003 Casciani et al.
6,665,385 B2 12/2003 Rogers et al.
6,694,177 B2 2/2004 Eggers et al.
6,699,194 B1 3/2004 Diab et al.
6,725,074 B1 4/2004 Kaestle
6,745,061 B1 6/2004 Hicks et al.
6,830,711 B2 6/2004 Mills et al.
6,801,137 B2 10/2004 Eggers
6,940,403 B2 9/2005 Kail, IV
7,018,338 B2 3/2006 Vetter et al.
7,027,858 B2 4/2006 Cao et al.
7,067,893 B2 6/2006 Mills et al.
7,099,715 B2 8/2006 Korzinov et al.
7,130,396 B2 10/2006 Rogers et al.
7,194,300 B2 3/2007 Korzinov
7,212,850 B2 5/2007 Prystowsky
7,215,984 B2 5/2007 Diab et al.
7,257,438 B2 * 8/2007 Kinast .......................... 600/509
7,332,784 B2 2/2008 Mills et al.
7,341,559 B2 3/2008 Schulz et al.
7,412,282 B2 8/2008 Houben
7,502,643 B2 3/2009 Farringdon et al.
7,553,166 B2 * 6/2009 Gobron .......................... 439/67
7,587,237 B2 9/2009 Korzinov et al.
7,668,588 B2 2/2010 Kovacs
7,729,753 B2 6/2010 Kremliovsky et al.
7,831,301 B2 11/2010 Webb et al.
7,881,765 B2 2/2011 Mertz et al.
D634,431 S 3/2011 Severe et al.
7,904,133 B2 3/2011 Gehman et al.
7,907,996 B2 3/2011 Prystowsky et al.
7,941,207 B2 5/2011 Korzinov
7,962,202 B2 6/2011 Bhunia
7,988,638 B2 8/2011 Novac
8,116,841 B2 2/2012 Bly et al.
8,145,287 B2 3/2012 Diab et al.
8,150,502 B2 4/2012 Kumar et al.
8,160,682 B2 4/2012 Kumar et al.
D659,836 S 5/2012 Bensch et al.
8,172,761 B1 5/2012 Rulkov et al.
8,200,319 B2 6/2012 Pu et al.
8,200,320 B2 6/2012 Kovacs
8,203,704 B2 6/2012 Merritt et al.
8,219,198 B2 7/2012 Gollasch et al.
8,249,686 B2 8/2012 Libbus et al.
8,271,072 B2 9/2012 Houben et al.
RE43,767 E 10/2012 Eggers et al.
8,285,356 B2 10/2012 Bly et al.
8,290,129 B2 10/2012 Rogers et al.
8,290,574 B2 10/2012 Field et al.
8,301,236 B2 10/2012 Baumann et al.
8,374,686 B2 2/2013 Ghanem
8,428,682 B1 4/2013 Rood et al.
8,452,364 B2 5/2013 Hannula et al.
8,460,189 B2 6/2013 Libbus et al.
8,473,039 B2 6/2013 Michelson et al.
8,473,047 B2 6/2013 Chakravarthy et al.
8,538,503 B2 9/2013 Kumar et al.
8,554,311 B2 * 10/2013 Warner et al. ................ 600/509
8,560,046 B2 10/2013 Kumar et al.
8,577,431 B2 11/2013 Lamego et al.
8,585,605 B2 11/2013 Sola I Caros et al.
8,591,430 B2 11/2013 Amurthur et al.
D701,964 S 4/2014 Yoneta et al.

(56) References Cited

U.S. PATENT DOCUMENTS 8,688,190 B2 4/2014 Libbus et al.
8,718,752 B2 5/2014 Libbus et al.
8,731,649 B2 5/2014 Lisogurski
8,821,397 B2 9/2014 Al-Ali et al.
D744,109 S 11/2015 Yoneta et al.
D744,110 S 11/2015 Kubo et al.
9,241,643 B2 1/2016 Lisogurski
9,277,864 B2 3/2016 Yang et al.
D760,903 S 7/2016 Lin et al.
9,392,946 B1 7/2016 Sarantos
9,506,802 B2 11/2016 Chu et al.
D787,066 S 5/2017 Kim et al.
9,636,057 B2 5/2017 Scheuing et al.
9,642,565 B2 5/2017 Gonopolskiy et al.
9,717,425 B2 8/2017 Kiani et al.
D800,313 S 10/2017 Chang
9,801,547 B2 10/2017 Yuen et al.
D810,944 S 2/2018 Goolkasian
D812,229 S 3/2018 Al-Siddiq
10,080,527 B2 9/2018 Golda et al.
2002/0038082 A1 3/2002 Chin
2003/0055478 A1 3/2003 Lyster
2003/0065269 A1 4/2003 Vetter et al.
2003/0073916 A1* 4/2003 Yonce .................. A61B 5/0428 600/509
2003/0149349 A1 8/2003 Jensen
2003/0176795 A1 9/2003 Harris et al.
2003/0225322 A1 12/2003 Uchiyama et al.
2004/0010201 A1 1/2004 Korzinov et al.
2004/0015091 A1 1/2004 Greenwald et al.
2004/0039419 A1 2/2004 Stickney et al.
2004/0039420 A1 2/2004 Jayne et al.
2004/0042581 A1 3/2004 Okerlund
2004/0082842 A1 4/2004 Lumba et al.
2004/0146149 A1 7/2004 Rogers et al.
2004/0260189 A1 12/2004 Eggers et al.
2005/0096557 A1 5/2005 Vosburgh
2005/0187466 A1 8/2005 Nordstrom
2005/0261559 A1* 11/2005 Mumford ............. A61B 5/0002 600/300
2005/0288726 A1 12/2005 Gollasch
2006/0167515 A1 7/2006 Stickney et al.
2006/0224072 A1 10/2006 Shennib
2007/0070800 A1 3/2007 Virag et al.
2007/0093705 A1 4/2007 Shin et al.
2007/0103296 A1 5/2007 Paessel et al.
2007/0106136 A1 5/2007 Sterling et al.
2007/0129642 A1 6/2007 Korzinov
2007/0130657 A1 6/2007 Rogers et al.
2007/0156054 A1 7/2007 Korzinov et al.
2007/0167850 A1 7/2007 Russell et al.
2007/0191723 A1 8/2007 Prystowsky et al.
2007/0191728 A1 8/2007 Shennib
2007/0255156 A1 11/2007 Mertz et al.
2007/0293776 A1 12/2007 Korzinov et al.
2008/0061846 A1* 3/2008 Kase .................. H03F 3/45192 327/108
2008/0139953 A1 6/2008 Baker et al.
2008/0288026 A1 11/2008 Cross
2008/0300641 A1 12/2008 Brunekreeft et al.
2009/0054742 A1 2/2009 Kaminska
2009/0076340 A1 3/2009 Libbus et al.
2009/0076341 A1 3/2009 James et al.
2009/0076342 A1 3/2009 Amurthur et al.
2009/0076344 A1 3/2009 Libbus et al.
2009/0076345 A1 3/2009 Manicka et al.
2009/0076346 A1 3/2009 James et al.
2009/0076349 A1 3/2009 Libbus et al.
2009/0076350 A1 3/2009 Bly et al.
2009/0076363 A1 3/2009 Bly et al.
2009/0076364 A1 3/2009 Libbus et al.
2009/0076397 A1 3/2009 Libbus et al.
2009/0076405 A1 3/2009 Amurthur et al.
2009/0076410 A1 3/2009 Libbus et al.
2009/0076559 A1 3/2009 Libbus et al.
2009/0105602 A1 4/2009 Gehman et al.
2009/0171177 A1 7/2009 Hannula et al.
2009/0234410 A1 9/2009 Libbus et al.
2009/0290279 A1 11/2009 Rodgriguez et al.
2010/0004518 A1 1/2010 Vo et al.
2010/0026995 A1 2/2010 Merritt et al.
2010/0030039 A1 2/2010 Lamego
2010/0054138 A1 3/2010 Gips et al.
2010/0134241 A1 6/2010 Gips et al.
2010/0179391 A1* 7/2010 Quintanar et al. ............ 600/301
2010/0191509 A1* 7/2010 Li et al. ........................ 702/191
2010/0198044 A1 8/2010 Gehman et al.
2010/0204586 A1 8/2010 Pu et al.
2010/0204599 A1 8/2010 Pu et al.
2010/0249541 A1 9/2010 Geva et al.
2010/0262430 A1 10/2010 Gips et al.
2010/0268103 A1 10/2010 Mcnamara et al.
2010/0286495 A1 11/2010 McGonigle et al.
2010/0286532 A1* 11/2010 Farringdon et al. .......... 600/483
2010/0298655 A1 11/2010 McCombie
2010/0298656 A1 11/2010 McCombie
2010/0312188 A1 12/2010 Robertson
2010/0317937 A1 12/2010 Kuhn et al.
2010/0317942 A1 12/2010 Cinbis et al.
2010/0317947 A1 12/2010 Cinbis et al.
2010/0318146 A1 12/2010 Cinbis et al.
2010/0324389 A1 12/2010 Moon et al.
2011/0021897 A1 1/2011 Webb et al.
2011/0066039 A1 3/2011 Banet et al.
2011/0066049 A1 3/2011 Matsumoto
2011/0098933 A1 4/2011 Ochs
2011/0105860 A1 5/2011 Houben et al.
2011/0105926 A1 5/2011 Kornet
2011/0124979 A1 5/2011 Heneghan
2011/0125040 A1* 5/2011 Crawford et al. ............ 600/509
2011/0144470 A1 6/2011 Mazar et al.
2011/0160604 A1* 6/2011 Istvan et al. .................. 600/509
2011/0166434 A1* 7/2011 Gargiulo ....................... 600/372
2011/0166468 A1 7/2011 Prystowsky et al.
2011/0190598 A1 8/2011 Shusterman
2011/0208076 A1* 8/2011 Fong et al. ................... 600/509
2011/0208078 A1 8/2011 Cho et al.
2011/0263994 A1 10/2011 Burns
2011/0270049 A1 11/2011 Katra et al.
2011/0270112 A1 11/2011 Manera et al.
2011/0279963 A1 11/2011 Kumar
2011/0301445 A9 12/2011 Webb et al.
2012/0016245 A1 1/2012 Niwa et al.
2012/0029306 A1 2/2012 Paquet
2012/0029320 A1 2/2012 Watson et al.
2012/0035490 A1 2/2012 Shen et al.
2012/0035494 A1 2/2012 Chakravarthy et al.
2012/0061695 A1 3/2012 Kim
2012/0071744 A1* 3/2012 Euliano et al. ............... 600/382
2012/0083673 A1 4/2012 Al-Ali et al.
2012/0101396 A1* 4/2012 Solosko ............... A61B 5/0006 600/509
2012/0108917 A1 5/2012 Libbus et al.
2012/0108920 A1 5/2012 Bly et al.
2012/0110226 A1 5/2012 Vlach et al.
2012/0110228 A1 5/2012 Vlach et al.
2012/0136226 A1 5/2012 Wilke
2012/0176599 A1 7/2012 Leung
2012/0197150 A1 8/2012 Cao et al.
2012/0203077 A1 8/2012 He et al.
2012/0204068 A1 8/2012 Ye et al.
2012/0226129 A1* 9/2012 Callahan et al. ............. 600/392
2012/0232369 A1* 9/2012 Kim et al. .................... 600/372
2012/0245951 A1 9/2012 Gips et al.
2012/0277549 A1 11/2012 Libbus et al.
2012/0284003 A1 11/2012 Gosh
2012/0289839 A1 11/2012 Takenoshita
2012/0330126 A1 12/2012 Hoppe
2013/0012938 A1* 1/2013 Asirvatham ....... A61B 5/04001 606/41
2013/0085347 A1 4/2013 Manicka et al.
2013/0096395 A1 4/2013 Katra et al.
2013/0116520 A1 5/2013 Roham
2013/0116534 A1 5/2013 Woo

(56) References Cited

U.S. PATENT DOCUMENTS

2013/0116585 A1 5/2013 Bouguerra
2013/0144130 A1 6/2013 Russell et al.
2013/0158372 A1 6/2013 Haisley
2013/0172724 A1 7/2013 Aziz et al.
2013/0225938 A1 8/2013 Vlach
2013/0225967 A1 8/2013 Esposito
2013/0245388 A1* 9/2013 Rafferty et al. .............. 600/301
2013/0245394 A1 9/2013 Brown et al.
2013/0253285 A1 9/2013 Bly et al.
2013/0267854 A1 10/2013 Johnson et al.
2013/0296660 A1 11/2013 Tsien
2013/0296823 A1 11/2013 Melker
2013/0324812 A1 12/2013 Brainard
2013/0324816 A1 12/2013 Bechtel et al.
2013/0324855 A1 12/2013 Lisogurski
2013/0331665 A1 12/2013 Libbus et al.
2013/0338448 A1 12/2013 Libbus et al.
2013/0338460 A1 12/2013 He et al.
2014/0038147 A1* 2/2014 Morrow ............... A61B 5/0478 434/236
2014/0066732 A1 3/2014 Addison et al.
2014/0066783 A1 3/2014 Kiani et al.
2014/0081152 A1 3/2014 Clinton
2014/0091926 A1 4/2014 Gips et al.
2014/0100432 A1 4/2014 Golda et al.
2014/0206976 A1 7/2014 Thompson
2014/0228656 A1 8/2014 Gonopolskiy et al.
2014/0275869 A1 9/2014 Kintz et al.
2015/0057511 A1 2/2015 Basu
2015/0087948 A1 3/2015 Bishay et al.
2015/0087951 A1 3/2015 Felix et al.
2015/0094551 A1 4/2015 Frix et al.
2015/0094552 A1 4/2015 Golda et al.
2015/0148622 A1 5/2015 Moyer et al.
2015/0148637 A1 5/2015 Golda et al.
2015/0148691 A1 5/2015 Moyer et al.
2015/0335288 A1 11/2015 Toth et al.
2015/0351690 A1 12/2015 Toth et al.
2016/0302674 A1 10/2016 Moyer et al.
2017/0027513 A1 2/2017 Mulpuru
2017/0095156 A1 4/2017 Richards

FOREIGN PATENT DOCUMENTS

CN 201641985 U 11/2010
CN 101984743 A 3/2011
CN 202288274 U 7/2012
EP 0581073 A2 2/1994
EP 2438851 A2 4/2012
JP H05123305 A 5/1993
JP H07213630 A 8/1995
JP H09224917 A 9/1997
JP 2001078974 A 3/2001
JP 2002125944 A 5/2002
JP 2002263075 A 9/2002
JP 2004016248 A 1/2004
JP 2006000481 A 1/2006
JP 2006158813 A 6/2006
JP 2007244531 A 9/2007
JP 2002263075 A 9/2009
JP 20120187404 A 10/2012
WO WO9401039 A1 1/1994
WO WO9427494 A1 12/1994
WO WO0045696 A1 8/2000
WO WO0059374 A1 10/2000
WO WO2001085019 A2 11/2001
WO WO2001093758 A1 12/2001
WO WO0200094 A2 1/2002
WO WO1002086837 A1 10/2002
WO WO2002085201 A1 10/2002
WO WO2002086792 A2 10/2002
WO WO2002086835 A1 10/2002
WO WO2003077752 A1 9/2003
WO WO2005079429 A2 1/2005
WO WO2005060829 A1 7/2005
WO WO2005072237 A2 8/2005
WO WO2006014806 A2 2/2006
WO WO2006044919 A2 4/2006
WO WO2006124788 A2 11/2006
WO WO2009036321 A1 3/2009
WO WO2009036327 A1 3/2009
WO 2009112972 A2 9/2009
WO WO2010093900 A2 8/2010
WO WO2010104952 A2 9/2010
WO WO2010107913 A2 9/2010
WO WO2011074004 A2 6/2011
WO WO2012104658 A2 8/2012
WO WO2012129498 A1 9/2012
WO WO2012150563 A1 11/2012

OTHER PUBLICATIONS

Timmerman, Luke, Xconomy, Inc., "UW Spinout Cardiac Insight Wins FDA OK for Heartbeat Monitor", published Jun. 6, 2013; website accessed Oct. 27, 2013, http://www.xconomy.com/seattle/2013/06/06/uw-spinout-cardiac-insight-wins-fda-ok-for-heartbeat-monitor/, Xconomy Inc., Cambridge, Massachusetts.

CardioNet, Inc., "CardioNet, Inc. Announces Launch of MCOTos 2:1 Device", published Jun. 19, 2013; website accessed Oct. 27, 2013, https://www.cardionet.com/index.htm, BioTelemetry, Inc., Conshohocken, Pennsylvania.

Heart Check, "The HeartCheck Pen, a Handheld ECG with SMART Monitoring", website accessed Oct. 27, 2013, http://heartcheckpen.com/,HeartCheckPEN.com, TAW Global, LLC, Portage, Michigan; CardioComm Solutions Inc., Toronto, ON, and Victoria, BC.

Corventis, Inc., "Nuvant Mobile Cardiac Telemetry", Copyright 2009-2013; website accessed Oct. 27, 2013, http://corventis.com/, Corventis, San Jose, California.

International Preliminary Report on Patentability dated Apr. 16, 2015 and International Preliminary Report on Patentability dated Apr. 7, 2015 with Written Opinion of the International Searching Authority International Application No. PCT/US2013/063748 issued by the United State Patent Office, dated Feb. 27, 2014, 5 pages, Alexandria, Virginia.

International Search Report and Written Opinion of the International Searching Authority. International Application No. PCT/US2015/13113 issued by the United State Patent Office, dated Jun. 29, 2015, 14 pages, Alexandria, Virginia.

Extended European Search Report including the Supplementary European Search Report (SESR) for Application No. EP13843561.5 issued by the European Patent Office, Munich, Germany dated Apr. 29, 2016.

International Search Report and Written Opinion of the International Searching Authority. International Application No. PCT/US2016/039374 issued by the United State Patent Office, dated Oct. 28, 2016, 14 pages, Alexandria Virginia.

International Search Report and Written Opinion—PCT/US2017/066805—ISA/US—dated Mar. 12, 2018—12 pages.

Transmittal of International Preliminary Report of Patentability and International Preliminary Report on Patentability for Application No. PCT/US2016/039374 issued by the International Bureau of WIPO, Geneva, Switzerland dated Dec. 26, 2017.

Extended European Search Report including the Supplementary European Search Report for Application No. EP15740972 issued by the European Patent Office, Munich, Germany dated Aug. 29, 2017.

Allen, John, Photoplethysmography and its application in clinical physiological measurement, Physiological Measurement, Feb. 20, 2007, pp. R1-R39, vol. 28, No. 3, IOP Publishing Ltd., Bristol, United Kingdom.

* cited by examiner

FIG. 5D

WEARABLE CARDIAC MONITOR

CROSS-REFERENCE TO RELATED APPLICATION(S)

This is a nonprovisional application claiming the benefit of and priority to the provisional application, U.S. 61/710,768 filed Oct. 7, 2012, the entire contents, teachings and suggestions thereof being incorporated herein by this reference as if fully set forth here.

BACKGROUND

Advances in electronics, sensor technology and materials science have revolutionized patient monitoring technologies. In particular, many light and wearable devices are becoming available for a variety of cardiac monitoring applications. However, improvements may yet be desired for robust wearable devices that provide effective data collection, in some cases also with increased patient convenience and comfort. Other alternatives may include developments in one or more of device attachment, size, flexibility, data transfer, among others.

Further alternatives for cardiac patients and their physicians may then include robust and convenient personal cardiac monitors that in some instances may collect and transfer long-term data as well as monitor events in real-time.

SUMMARY

Described herein are several medical monitoring devices and systems, in some instances for long-term sensing and/or recording of cardiac patient data. A number of alternative implementations and applications are summarized and/or exemplified herein below and throughout this specification.

These as well as other aspects are exemplified in a number of illustrated alternative implementations and applications, some of which are shown in the figures and characterized in the claims section that follows. However, as will be understood by the ordinarily skilled artisan, the above summary and the detailed description below do not describe the entire scope of the inventions hereof and are indeed not intended to describe each illustrated embodiment or every implementation of the present inventions nor provide any limitation on the claims or scope of protection herein set forth below.

BRIEF DESCRIPTION OF THE DRAWINGS

The drawings include:

FIG. 1, which includes sub-part

DETAILED DESCRIPTION

Figure 1A:
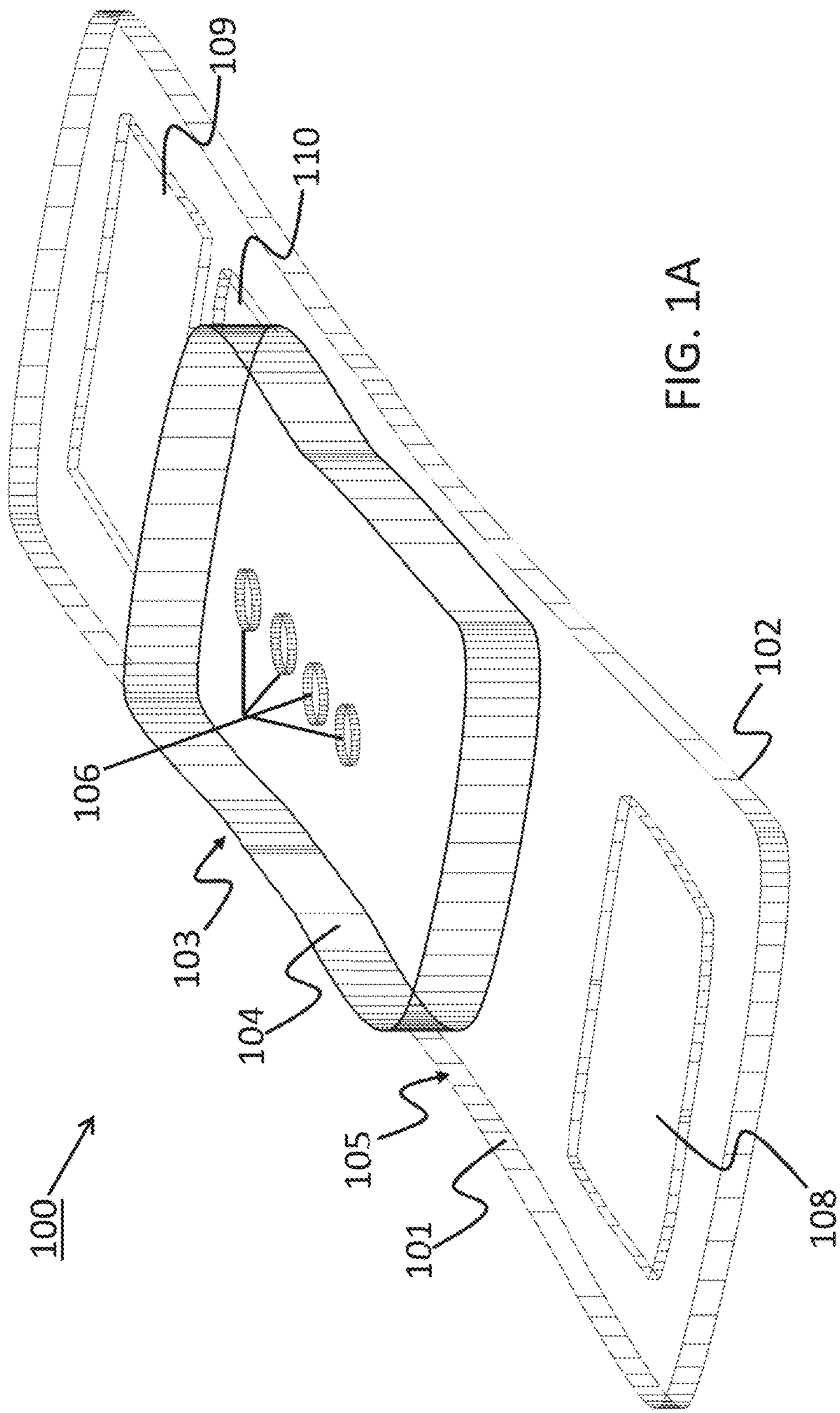
FIGS. 1A-1G, illustrates several alternatives of the present inventions, including various of isometric, top and bottom plan and elevational views of devices and alternative conductive adhesive structures.

While the inventions hereof amenable to various modifications and alternative forms, specifics thereof have been shown by way of example in the drawings and the following description. It should be understood, however, that the intention is not to limit the invention to the particular embodiments described. The intention is to cover all modifications, equivalents, and alternatives falling within the spirit and scope of the invention whether described here or otherwise being sufficiently appreciable as included herewithin even if beyond the literal words hereof.

In one aspect, a system hereof may include a device for monitoring physiological parameters such as one or more or all of electrocardiogram (aka ECG or EKG), photoplethysmogram (aka PPG), pulse oximetry and/or patient acceleration or movement signals. Systems hereof may be established to measure and process such signals of a patient using or including one or more of the following elements: (a) a circuit, sometimes flexible, embedded in a flat elastic substrate having a top surface and a bottom surface, the circuit having (i) at least one sensor mounted in or adjacent the bottom surface of the flat elastic substrate, the at least one sensor being capable of electrical or optical communication with the patient, (ii) at least one signal processing module for receiving and/or accepting signals from the at least one sensor in some implementations also providing for transforming such signals for storage as patient data; (iii) at least one memory module for receiving and/or accepting and storing patient data, (iv) at least one data communication module for transferring stored patient data to an external device, and (v) a control module for controlling the timing and operation of the at least one sensor, one or more of the at least one signal processing module, the at least one memory module, the at least one data communication module, and/or the control module capable of receiving commands to implement transfer of patient data by the at least one data communication module and to erase and/or wipe patient data from the at least one memory module; and (b) a anisotropically conductive adhesive removably attached to the bottom surface of the flat elastic substrate, the anisotropically conductive adhesive capable of adhering to skin of the patient and of conducting an electrical signal substantially only in a direction perpendicular to the bottom surface of the flat elastic substrate, and/or in some implementations including a conductive portion adjacent the sensor or sensors and a non-conductive portion.

In some implementations, devices hereof will be for comprehensive long-term cardiac monitoring. Features of such may include one or more of a Lead 1 ECG, PPG, pulse oximeter, accelerometer, and a button or other indicator for manual patient event marking. Such a device may be adapted to store up to, for example, about two weeks of continuous data (though more will also be feasible in alternative implementations), which may in some implementations be downloaded to a clinic or other computer in a short time period, as for one example, in only about 90 seconds (though less time will be viable in alternative implementations) via computer connection, whether wireless or wired as in one example by USB or other acceptable data connection. A companion software data analysis package may be adapted to provide automated event capture and/or allow immediate, local data interpretation.

Intermittent cardiac anomalies are often difficult for physicians to detect and/or diagnose, as they would typically have to occur during a physical examination of the patient. A device hereof may address this problem with what in some implementations may be a continuous or substantially continuous monitoring of a number of vital signs.

Some alternative features may include (i) a driven "Right Leg" circuit with electrodes located only on the chest, (ii) a "z-Axis" or anisotropic conductive adhesive electrode interface that may permit electrical communication only between an electrode and a patient's skin immediately beneath the electrode, (iii) data transmission to and interpretation by a local computer accessible to CCU/ICU personnel, (iv) a unique combination of hardware allows correlation of multiple data sources in time concordance to aid in diagnosis.

In some alternative implementations, devices and systems hereof may provide 1) reusability (in some cases near or greater than about 1000 patients) allows recouping cost of the device in just about 10-15 patient tests, 2) one or more of ecg waveform data, inertial exertion sensing, manual event marking, and/or pulse oximeter, any or all of which in time concordance to better detect and analyze arrhythmic events, 3) efficient watertightness or waterproofing (the patient can even swim while wearing the device), and 4) a comprehensive analysis package for immediate, local data interpretation. An alternative device may be adapted to take advantage of flex-circuit technology, to provide a device that is light-weight, thin, durable, and flexible to conform to the patient's skin.

FIGS. 1 and 2 illustrate examples of alternative implementations of devices that may be so adapted.

FIG. 1 shows a device 100 that has a component side or top side 101, patient side or circuit side 102, and one or more inner electrical layer(s), generally identified by the reference 103 and an elongated strip layer 105. The strip layer 105 may have electronics thereon and/or therewithin. FIG. 1A shows isometrically these together with some other elements that may be used herewith. FIG. 1B is more specifically directed to a top side 101 plan view and FIG. 1C to an underside, patient side 102 plan view and FIG. 1D a first elevational, side view.

Figure 1B:
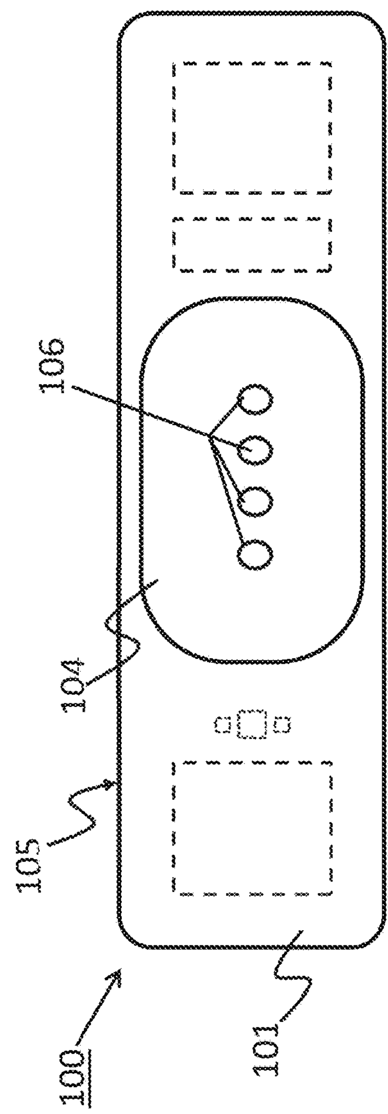
Figure 1C:
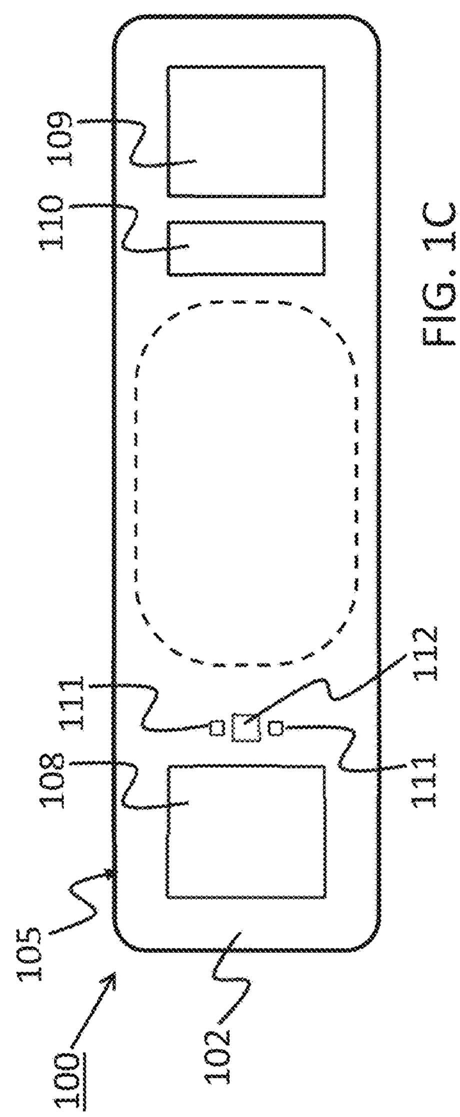
Figure 1D:
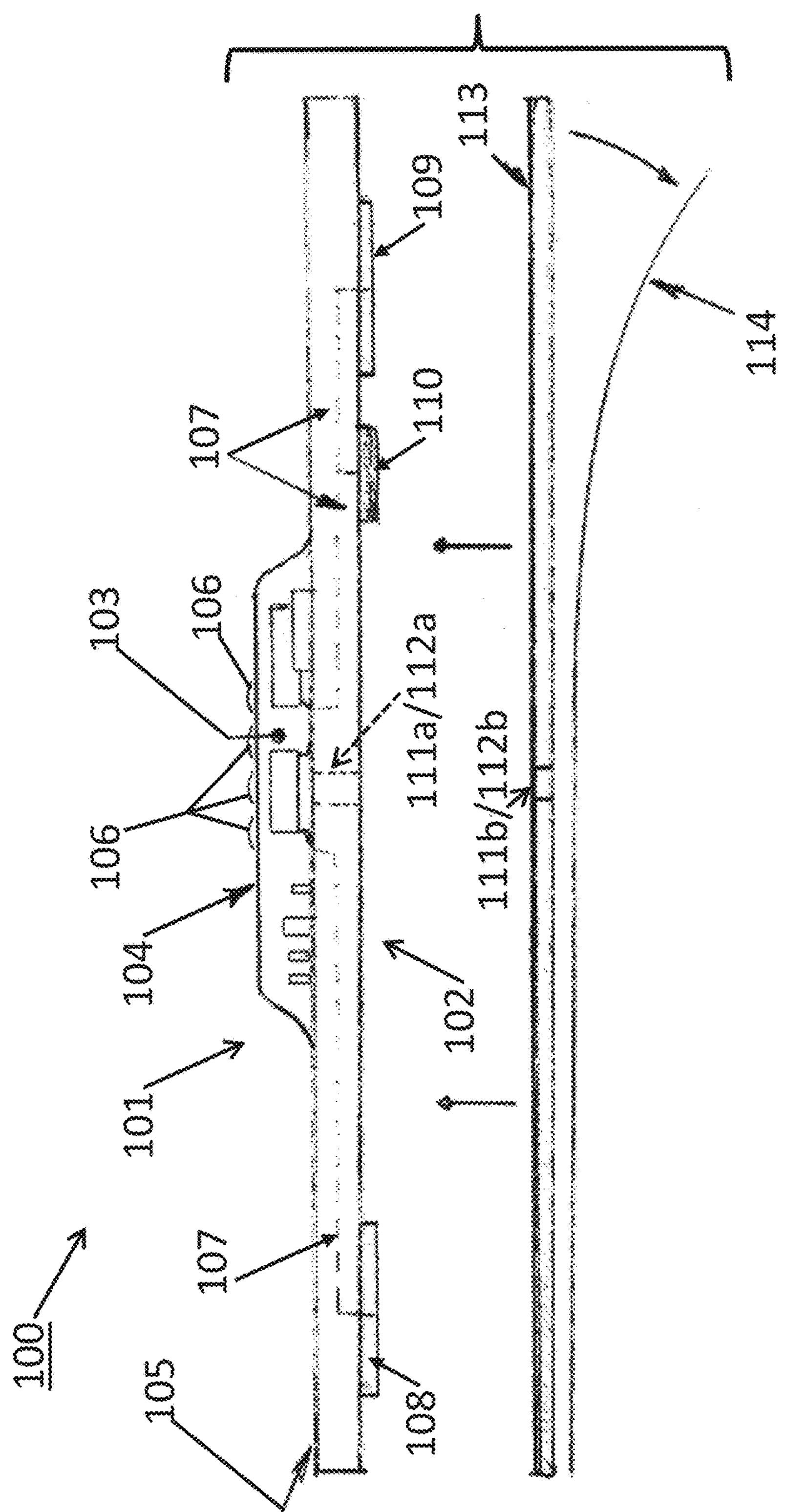

Many of the electronics hereof may be disposed in the electronics layer or layers 103, and as generally indicated here, the electronics may be encapsulated in a material 104 (see FIGS. 1A, 1B and 1D for some examples), plastic or the like, or potting material, to fix them in operative position on or in or otherwise functionally disposed relative to the elongated strip layer 105. The potting or other material may in many implementations also or alternatively provide a waterproof or watertight or water resistant coverage of the electronics to keep them operative even in water or sweat usage environments. One or more access points, junctions or other functional units 106 may be provided on and/or through any side of the encapsulation material 104 for exterior access and/or communication with the electronics disposed therewithin, or thereunder. FIGS. 1A, 1B and 1D show four such accesses 106 on the top side. These may include high Z data communication ports and/or charging contacts, inter alia. This upper or component side 101 of device 100 may be coated in a silicone compound for protection and/or waterproofing, with only, in some examples, a HS USB connector exposed via one or more ports 106, e.g., for data communication or transfer and/or for charging.

The elongated strip layer 105 may be or may include a circuit or circuit portions such as electrical leads or other inner layer conductors, e.g., leads 107 shown in FIG. 1D, for communication between the electronics 103 and the electrically conductive pads or contacts 108, 109 and 110 described further below (108 and 109 being in some examples, high impedance/high Z silver or copper/silver electrodes for electrocardiograph, ECG, and 110 at times being a reference electrode). In many implementations, the strip layer 105 may be or may include flex circuitry understood to provide acceptable deformation, twisting, bending and the like, and yet retain robust electrical circuitry connections therewithin. Note, though the electronics 103 and electrodes 108, 109, 110 are shown attached to layer 105; on top for electronics 103, and to the bottom or patient side for electrodes 108, 109, 110; it may be that such elements may be formed in or otherwise disposed within the layer 105, or at least be relatively indistinguishably disposed in relative operational positions in one or more layers with or adjacent layer 105 in practice. Similarly, the leads or traces 107 are shown embedded (by dashed line representation in FIG. 1D); however, these may be on the top or bottom side, though more likely top side to insulate from other skin side electrical communications. If initially top side (or bottom), the traces may be subsequently covered with an insulative encapsulant or like protective cover (not separately shown), in many implementations, a flexible material to maintain a flexible alternative for the entire, or majority of layer 105.

On the patient side 102, the ECG electrodes 108, 109 and 110 may be left exposed for substantially direct patient skin contact (though likely with at least a conductive gel applied therebetween); and/or, in many implementations, the patient side electrodes 108, 109 and/or 110 may be covered by a conductive adhesive material as will be described below. The electrodes may be or may be may be plated with a robust high conductive material, as for example, silver/silver chloride for biocompatibility and high signal quality, and in some implementations may be highly robust and, for one non-limiting example, be adapted to withstand over about 1000 alcohol cleaning cycles between patients. Windows or other communication channels or openings 111, 112 may be provided for a pulse oximeter, for example, for LEDs and a sensor. Such openings 111, 112 would typically be disposed for optimum light communication to and from the patient skin. An alternative disposition of one or more light conduits 111*a*/112*a* is shown in a non-limiting example in FIG. 1D more nearly disposed and/or connected to the electronics 103. A variety of alternative placements may be usable herein/herewith.

FIG. 1D provides a first example of an adhesive 113 that may be used herewith. The adhesive layer 113 is here a double-sided adhesive for application to the bottom side 102 of the device 100, and a second side, perhaps with a different type of adhesive for adhering to the skin of the human patient (not shown). Different types of materials for adhesion might be used in that the material of choice to which the adhesive layer is to be attached are different; typically, circuit or circuit board material for connection to the device 100, and patient skin (not separately shown) on the patient side. A protective backing 114 may be employed on the patient side until application to the patient is desired. Note, in many applications, the adhesive 113 is anisotropic in that it may preferably be only conductive in a single or substantially a single direction, e.g., the axis perpendicular to the surface of adhesive contact. Thus, good electrically conductive contact for signal communication can be had through such adhesive to/through the adhesive to the electrical contacts or electrodes, 108, 109 and 110. Note, a corresponding one or more light apertures 111*b*/112*b* are shown in the adhesive of 113 of the example of FIG. 1D to communicate light therethrough in cooperation with the light conduit(s) 111*a*/112*a* in/through layer 105 for communication of light data typically involved in pulse oximetry.

The adhesive may thus be placed or disposed on the device 100, in some implementations substantially permanently, or with some replaceability. In some implementations, the device as shown in FIGS. 1A-1D and/or 1G without (or with in some implementations) the adhesive may be reusable. In many such cases, the adhesive layer 113 may be removed and replaced before each subsequent use, though subsequent re-use of and with a layer 113 is not foreclosed. In a first or subsequent use with a replaceable adhesive layer 113, it may be that the user applying the device to the patient, e.g., the physician or technician or even the patient, him/herself, applies the conductive transfer adhesive 113 to the patient side 102 of the device 100. The protective backing 114 may then be removed, and the device adhered to the patient and activated. Activation may occur in a number of ways; in some, it may be pre-set that an affirmative activation interaction may not be necessary from the doctor or patient or like due to either an inertial and/or a pulse oximeter activation which may be substantially automatically activating, e.g., upon receiving sufficient minimum input (movement in case of inertial system or light reflection of blood flow for pulse oximetry); however, a button may be provided at access 106 or in some other location adjacent the electronics to allow the patient to start or stop the device or otherwise mark an event if desired. In one exemplar implementation the device may be worn for a period such as two weeks for collection of data substantially continuously, or at intervals as may be preferred and established in or by the systems hereof.

After a monitoring period is over a physician, technician, patient or other person may then remove the device from the patient body, remove the adhesive, in some instances with alcohol, and may establish a data communication connection for data transfer, e.g., by wireless communication or by insertion/connection of a USB or like data connector to download the data. The data may then be processed and/or interpreted and in many instances, interpreted immediately if desired. A power source on board may include a battery and this can then also be re-charged between uses, in some implementations, fully recharged quickly as within about 24 hours, after which the device could then be considered ready for the next patient.

Figure 1E:
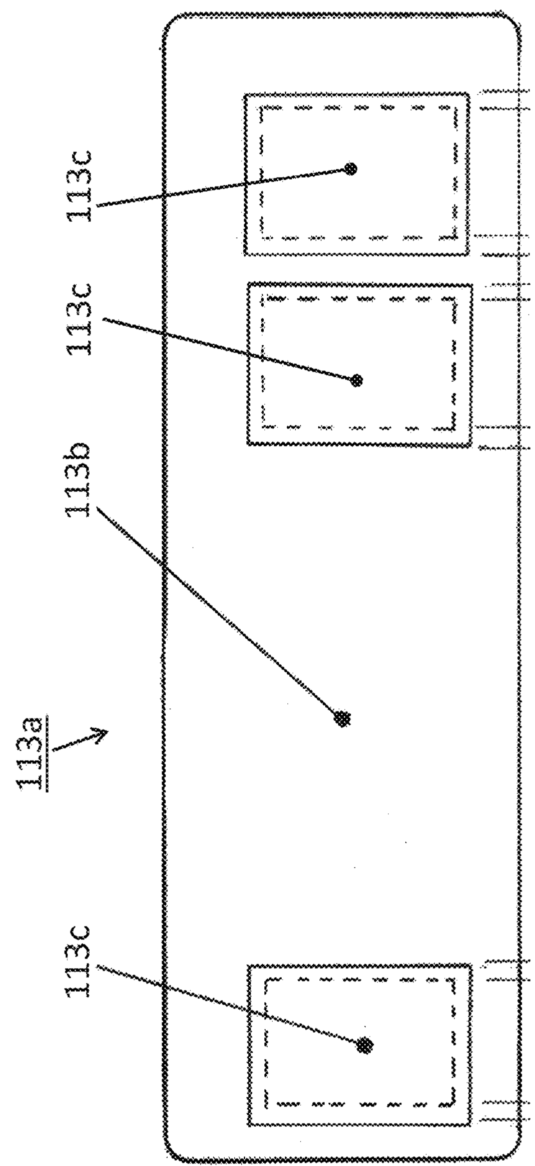
Figure 1F:
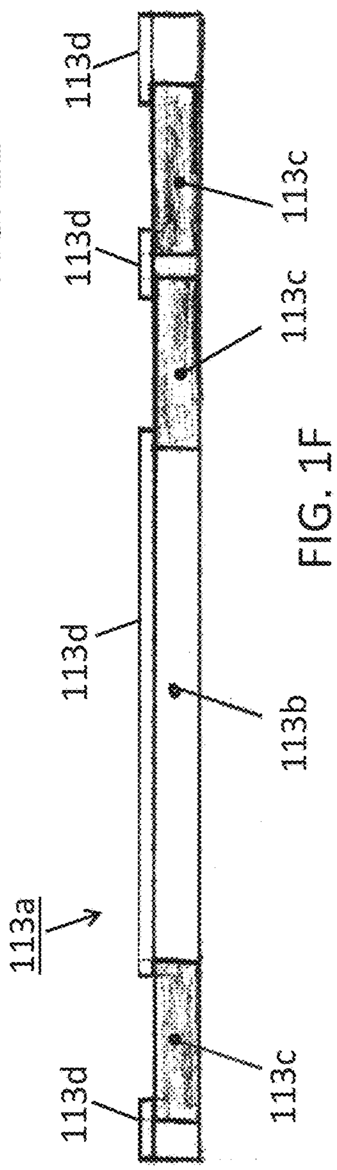
Figure 1G:
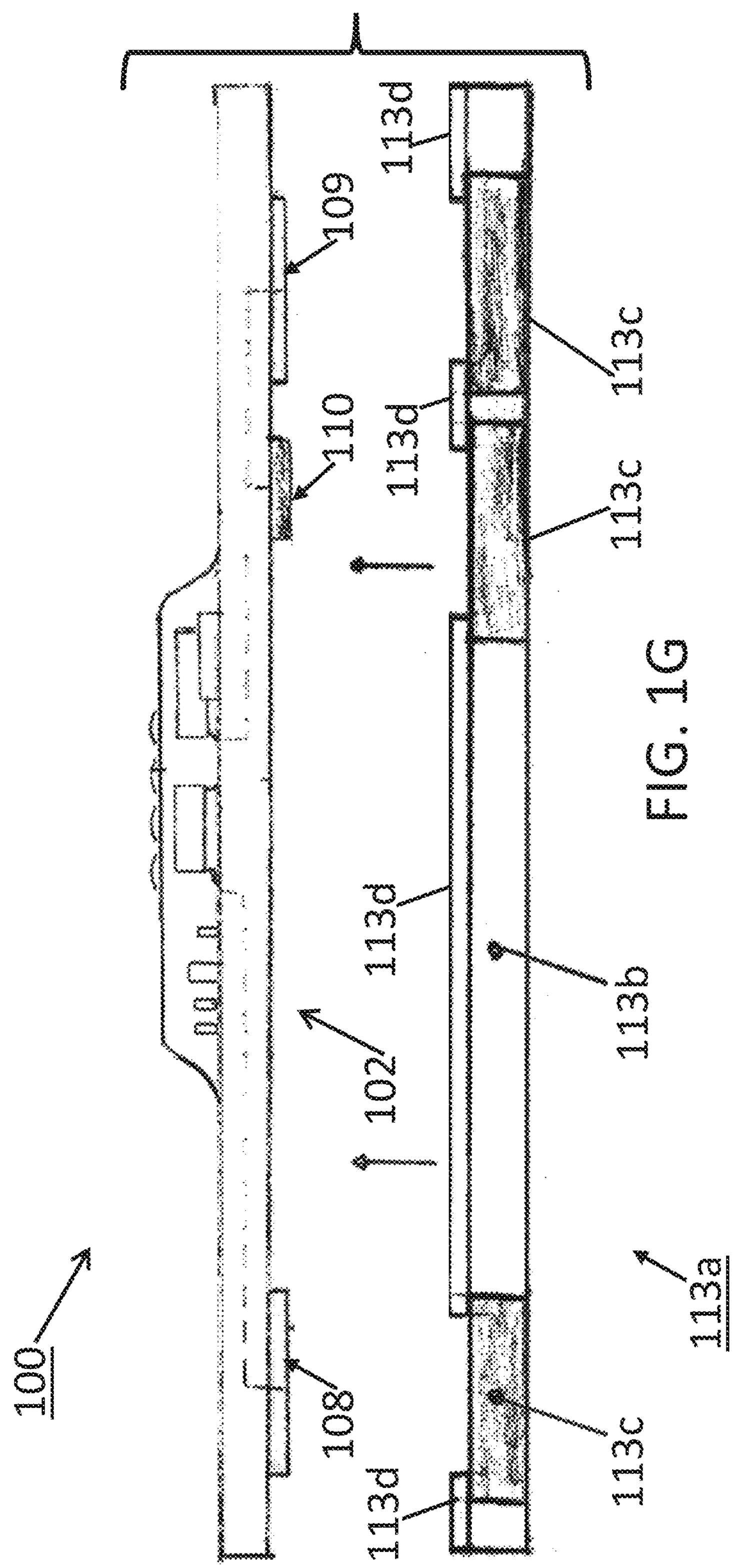

Some alternative conductive adhesives may be used herewith. FIGS. 1E, 1F and 1G show one such alternative conductive adhesive 113*a*; a bottom plan view in FIG. 1E and elevational side views thereof in FIGS. 1F and 1G (as being connected to a device 100 in FIG. 1G). In some implementations, the conductivity may be anisotropic as introduced above; in some conductive primarily if not entirely in the direction of the Z-Axis; perpendicular to the page (into and/or out of the page) in FIG. 1E, and/or vertically or transversally relative to the long horizontal shown axis of device 100 in the implementation view of FIG. 1F.

The implementation of this particular example includes a composite adhesive 113*a* which itself may include some non-conductive portion(s) 113*b* and some one or more conductive portions 113*c*. The adhesive composite 113*a* may, as described for adhesive 113 above be double sided such that one side adheres to the patient while the other side would adhere to the underside 102 of the device 100 (see FIG. 1G) so that one or more conductive portions 113*c* may be disposed or placed in electrically communicative and/or conductive contact with the integrated electrodes on the electronic monitoring device 100. Since the electrodes would operate better where they may be electrically isolated or insulated from each other, yet each making electrical contact or communication with the patient's skin, the adhesive may further be more specifically disposed in some implementations as follows.

As shown in FIGS. 1E and 1F, three isolated conductive portions 113*c* may be disposed separated from each other by a body portion 113*b* which may be non-conductive. These could then correspond to the electrodes 108, 109, 110 from the above-described examples, and as more particularly shown schematically in FIG. 1G (note the scale is exaggerated for the adhesive 113*a* and thus, exact matching to the electrodes of device 100 is not necessarily shown). In some examples, the electrode areas 113*c* may be a conductive hydrogel that may or may not be adhesive, and in some examples, may be made of a conductive an adhesive conductive material such as 3M Corporation 9880 Hydrogel adhesive (3M Company, St. Paul, Minn.). These areas 113*c* may then be isolated from each other by a non-conductive material 113*b* such as 3M Corporation 9836 tape or 3M double-sided Transfer Adhesive 9917 (3M, St. Paul, Minn.) or equivalent. The additional layer 113*d*, if used, might be a 3M 9917 adhesive together with the 113*b* of a 9836 material. These constructs may provide the effect of creating a low electrical impedance path in the Z-axis direction (perpendicular to page for FIG. 1E and vertically/transversally for FIGS. 1F and 1G) for the electrode areas 113*c*, and high electrical impedance path between the electrodes in the X/Y directions. (See FIGS. 1E, 1F and 1G; coplanar with the page in FIG. 1E and horizontal and perpendicular to the page in FIGS. 1F and 1G). Thus, a composite adhesive strip can ensure not only device adhering to the patient, but also that the electrodes whether two or as shown three electrodes are conductively connected by conductive portions of the adhesive strip, where the combination of conductive and non-conductive portions can then reduce signal noise and/or enhance noise free characteristics. Electrodes that move relative to skin can introduce noise. I.e., electrodes electrically communicative/connected to the skin via a gel may move relative to the skin and thus introduce noise. However, with one or more conductive adhesive portions in a composite adhesive connected to respective electrodes and then substantially securely connected to the skin will keep the respective electrodes substantially fixed relative to the skin and thereby reduce or even eliminate electrode movement relative to the skin. Removal of such movement would then remove noise which would thereby provide a clean signal that can allow for monitoring cardiac P waves which enhances the possibility to detect arrythmias that couldn't otherwise be detected. Further description is set forth below.

In some implementations, a further optional connective and/or insulative structure 113*d* may be implemented as shown in FIG. 113*d* to provide further structural and insulative separation between electrodes with connected to a device 100 on the underside 102 thereof (see FIG. 1G). Though shown separate in FIGS. 1F and 1G, it may be contiguous with the insulative adhesive 113*b* of these views.

Some alternative implementations hereof may include a driven right leg ECG circuit with one or more chest only electrodes ("Driven Chest Electrode"). In addition to the electrodes used to measure a single or multiple lead electrocardiogram signal, a device 100 may use an additional electrode, as for example the reference electrode 110 (see FIGS. 1A, 1C, 1D and 1G, e.g.) to reduce common mode noise. Such an electrode may function in a manner similar to the commonly-used driven right leg electrode, but may here be located on the patient's chest rather than on the patient's right leg but nevertheless this third/reference electrode may play the role of the leg electrode. This chest electrode may thus mimic a right leg electrode and/or be considered a proxy driven right leg electrode. A circuit, or portion of an overall circuit, adapted to operate in this fashion may include a number of amplifier stages to provide gain, as well as filtering to ensure circuit stability and to shape the overall frequency response. Such a circuit may be biased to control the common mode bias of the electrocardiogram signal. This driven chest electrode implementation may be used in conjunction with a differential or instrumentation amplifier to reduce common mode noise. In this case, the sense electrode may be used as one of the electrocardiogram electrodes. Alternatively, a single-ended electrocardiogram amplifier may be used where the differential electrocardiogram signal is referenced to ground or to some other known voltage.

Figure 2A:
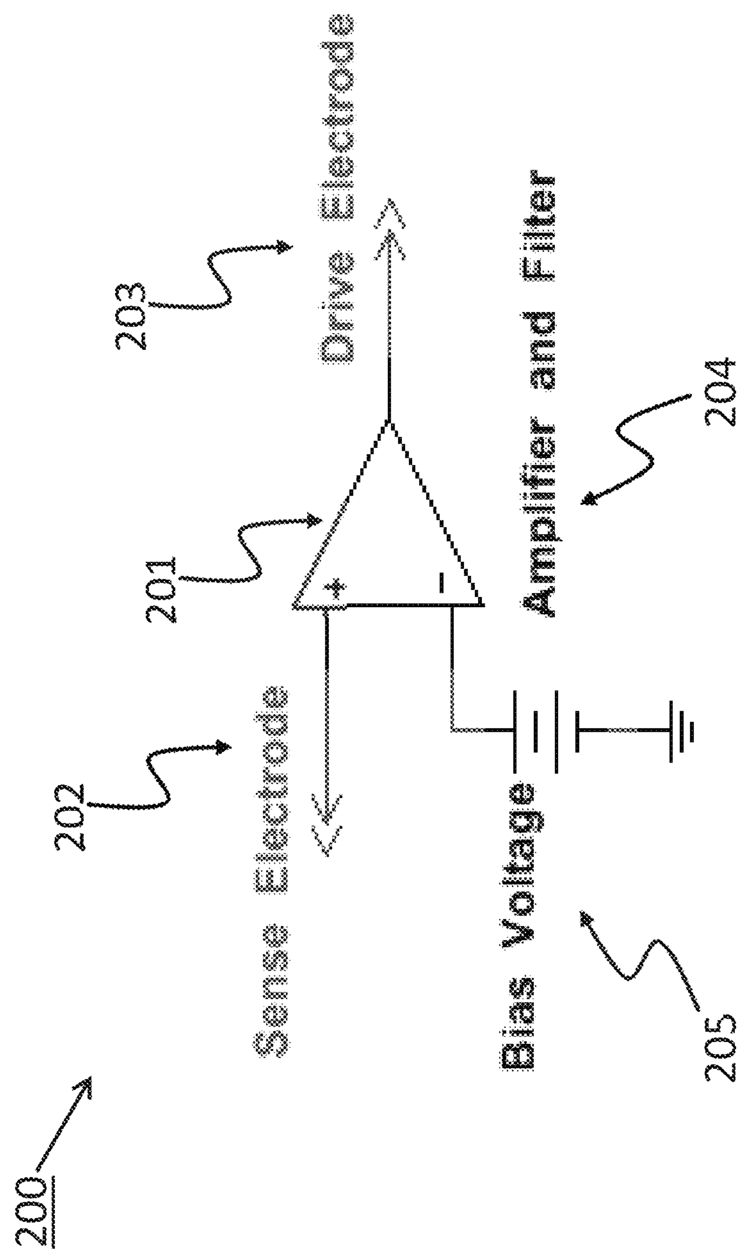
FIG. 2, which includes sub-part FIGS. 2A-2C, provides circuit diagrams of alternatives to a driven right leg circuit.

A circuit or sub-circuit 200 using a transistor 201 as shown in FIG. 2 may be such a circuit (aka module) and may thus include as further shown in FIG. 2A, a sense electrode 202, a drive electrode 203, and an amplifier 204. Both the sense and drive electrodes 202, 203 are placed on the patient's chest such that they provide an electrical connection to the patient. The amplifier 204 may include gain and filtering. The amplifier output is connected to the drive electrode, the inverting input to the sense electrode, and the non-inverting input to a bias voltage 205. The amplifier maintains the voltage of the sense electrode at a level close to the bias voltage. An electrocardiogram signal may then be measured using additional electrodes. Indeed, as was the case for the improved conductivity through use of anisotropic adhesive portions above, here also or alternatively, the use of this third electrode as a proxy for a right leg electrode (i.e., proxy driven right leg electrode) can provide signal reception otherwise unavailable. Clean signals may thus allow for receiving cardiac P waves which enhances the possibility to detect arrythmias that couldn't otherwise be detected.

Figure 2C:
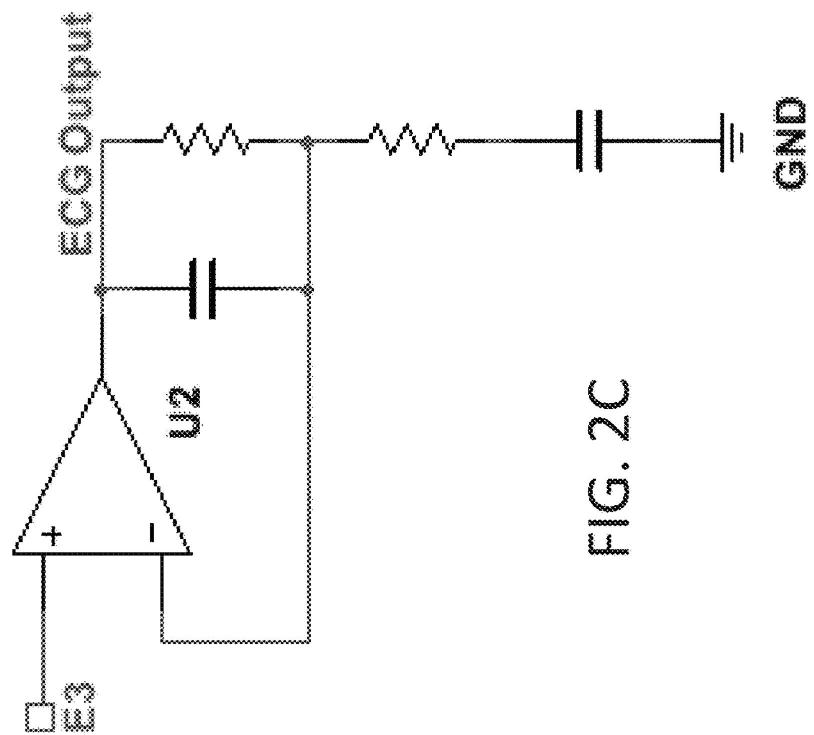
Figure 2B:
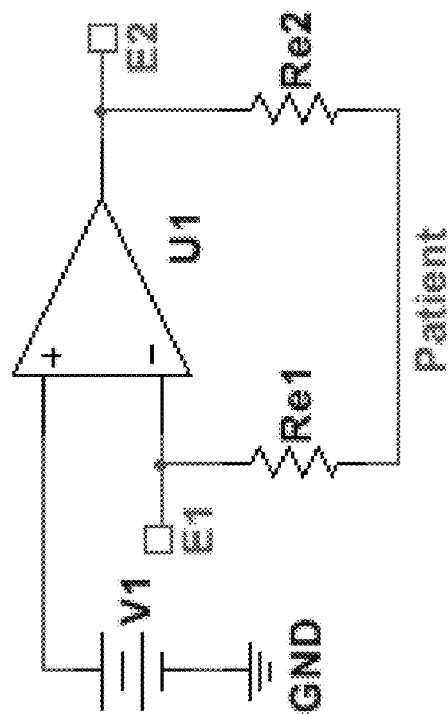

Further alternative descriptions of circuitry include that which is shown in FIGS. 2B and 2C; in which are shown non-limiting alternatives in which three adjacent electrodes E1, E2, and E3 may be used to pick up the ECG signal, one of which electrodes playing the role of the distant limb electrode of traditional ECG monitors. Because the electrode-patient interface has an associated impedance (Re1 and Re2), current flowing through this interface will cause a difference in voltage between the patient and the electrode. The circuit may use a sense electrode (E1) to detect the patient voltage. Because this exemplar circuit node has a high impedance to circuit ground (GND), very little current flows through the electrode interface, so that the voltage drop between the patient and this node is minimized. The first of these alternative, non-limiting circuits (FIG. 2B) also contains an amplifier (U1) whose low-impedance output is connected to a separate drive electrode (E2). The amplifier uses negative feedback to control the drive electrode such that the patient voltage (as measured by the sense electrode E1) is equal to the bias voltage (V1). This may effectively maintain the patient voltage equal to the bias voltage despite any voltage difference between the driven electrode (E2) and the patient. This can include voltage differences caused by power line-induced current flowing between the drive electrode and the patient (through Re2). This arrangement differs from a traditional 'driven-right-leg' circuit in at least two ways: the driven electrode is placed on the patient's chest (rather than the right leg), and the ECG signal is a single-ended (not differential) measurement taken from a third electrode (E3). Because all electrodes are located on the patient's chest, a small device placed there may contain all the necessary electrodes for ECG measurement. One possible benefit of the single-ended measurement is that gain and filtering circuitry (U2 and associated components (FIG. 2C)) necessary to condition the ECG signal prior to recording (ECG Output) requires fewer components and may be less sensitive to component tolerance matching. The examples of FIGS. 2A, 2B and 2C are non-limiting examples and not intended to limit the scope of the claims hereto as other circuits with other circuit elements can be formed by skilled artisans in view hereof and yet remain within the spirit and scope of claims hereof.

In many implementations, a system hereof may include other circuitry operative together with the ECG electrodes, which may thus be accompanied by other sensors to provide time concordant traces of: i) ECG p-, qrs-, and t-waves; ii) O2 Saturation, as measured by Pulse Oxymetry; and/or iii) xyz acceleration, to provide an index of physical activity. Such circuitry may be implemented to one or more of the following electrical specifications. The overall system might in some implementations include as much as two weeks (or more) of continuous run time; gathering data during such time. Some implementations may be adapted to provide as many or even greater than 1000 uses. Alternatives may include operability even after or during exposure to fluids or wetness; in some such examples being water resistant, or waterproof, or watertight, in some cases continuing to be fully operable when fully submerged (in low saline water). Other implementations may include fast data transfer, as for an example where using an HS USB for full data transfer in less than about 90 seconds. A rechargeable battery may typically be used.

A further alternative implementation may include an electronic "ground": In a device hereof, mounted entirely on a flexible circuit board, the ground plane function may be provided by coaxial ground leads adjacent to the signal leads. The main contribution of this type of grounding system may be that it may allow the device the flexibility required to conform and adhere to the skin.

For electrocardiograph; EKG or ECG, some implementations may include greater than about 10 Meg Ohms input impedance; some implementations may operate with a 0.1-48 Hz bandwidth; and some with an approximate 256 Hz Sampling Rate; and may be implementing 12 Bit Resolution. For PPG and Pulse Oximeter, operation may be with 660 and 940 nm Wavelength; about 80-100 SpO2 Range; a 0.05-4.8 Hz Bandwidth; a 16 Hz Sampling Rate; and 12 bit resolution. For an accelerometer: a 3-Axis Measurement may be employed, and in some implementations using a ±2 G Range; with a 16 Hz Sampling Rate; and a 12 Bit Resolution.

Figure 3:
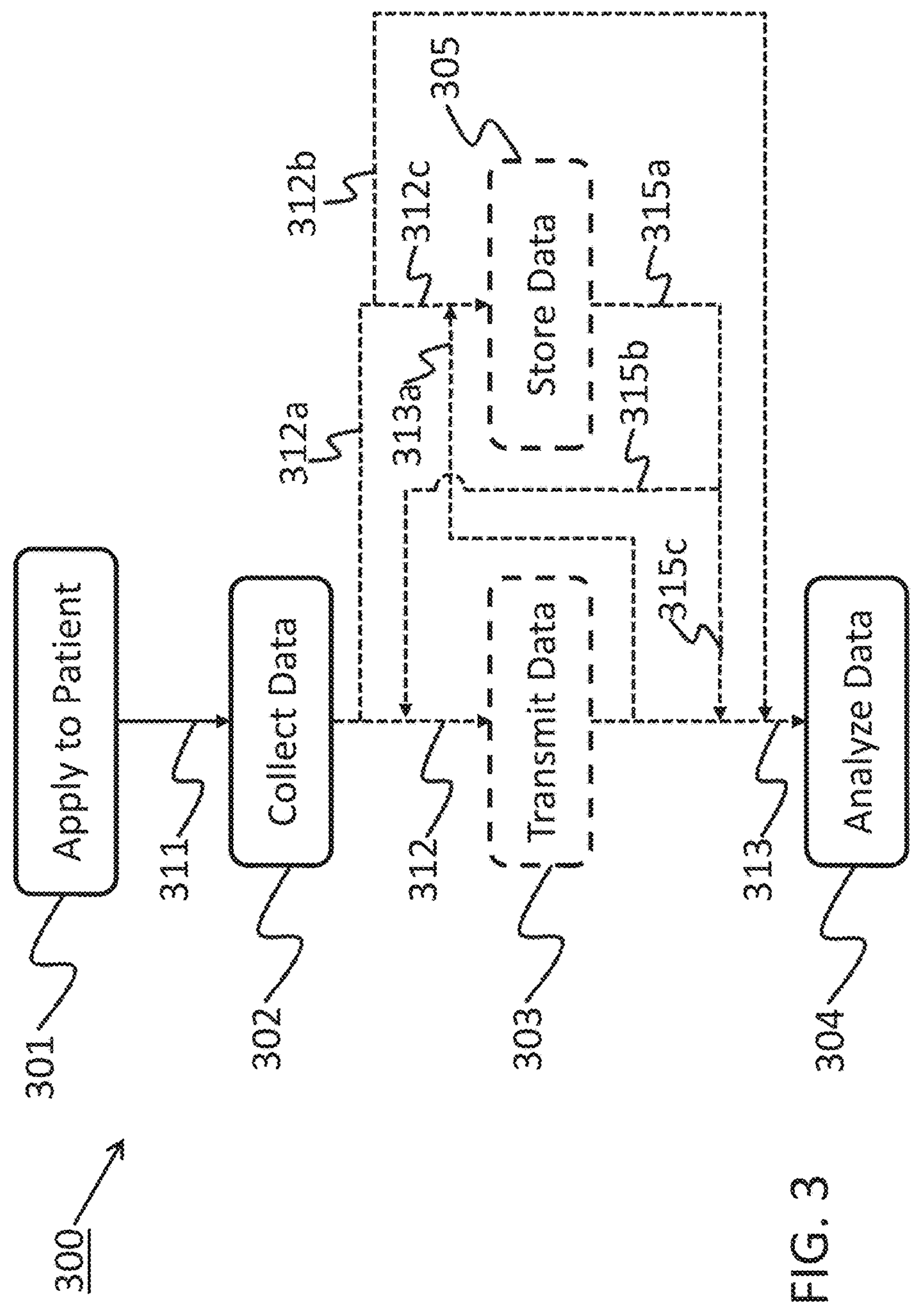
FIG. 3 is a flow chart including alternative methods of use.

Some summary methodologies may now be understood with relation to FIG. 3, though others may be understood through and as parts of the remainder of the disclosure hereof. A flow chart 300 as in FIG. 3 may demonstrate some of the alternatives; where an initial maneuver 301 might be the application of the device 100 to the patient. Indeed, this might include some one or more of the alternatives for adhesive application as described here above, whether by/through use of an adhesive such as that 113 of FIG. 1D, or that of FIGS. 1E, 1F and/or 1G. Then, as shown, in moving by flow line 311, a data collection operation 302 may be implemented. Note, this might include a continuous or substantially continuous collection or an interval or periodic collection or perhaps even a one time event collection. This may depend upon the type of data to be collected and/or be dependent upon other features or alternatives, as for example whether a long term quantity of data is desired, for ECG for example, or whether for example a relative single data point might be useful, as in some cases of pulse oximetry (sometimes a single saturation point might be of interest, as for example, if clearly too low, though comparison data showing trending over time, may indeed be more typical).

Several alternatives then present in FIG. 3, flow chart 300; a first such might be the following of flowline 312 to the transmission of data operation 303, which could then involve either wireless or wired (e.g., USB or other) data communication from the device 100 to data analysis and/or storage devices and/or systems (not separately shown in FIG. 3; could include computing devices, see e.g., FIG. 4 described below, or the like). Options from this point also appear; however, a first such might include following flow line 313 to the data analysis operation 304 for analyzing the data for determination of the relative health and/or for condition diagnosis of a patient. Computing systems, e.g., a computer (could be of many types, whether hand-held, personal or mainframe or other; see FIG. 4 and description below) could be used for this analysis; however, it could be that sufficient intelligence might be incorporated within the electronics 103 of device 100 such that some analysis might be operable on or within device 100 itself. A non-limiting example, might be a threshold comparison, as for example relative to pulse oximetry where when a low (or in some examples, perhaps a high) threshold level is reached an indicator or alarm might be activated all on/by the electronics 103 of the device 100.

A similar such example, might be considered by the optional alternative flow path 312*a* which itself branches into parts 312*b* and 312*c*. Following flow path 312 *a*, and then, in a first example path 312*b*, a skip of the transmit data operation 303 can be understood whereby analysis 304 might be achieved without substantial data transfer. This could explain on board analysis, whether as for example according to the threshold example above, or might in some instances include more detailed analysis depending upon how much intelligence is incorporated on/in the electronics 103. Another view, is relative to how much transmission may be involved even if the transmission operation 303 is used; inasmuch as this could include at one level the transmission of data from the patient skin through the conductors 108, 109 and/or 110 through the traces 107 to the electronics 103 for analysis there. In other examples, of course, the transmission may include off-board downloading to other computing resources (e.g., FIG. 4). In some cases, such off-loading of the data may allow or provide for more sophisticated analysis using higher computing power resources.

Further alternatives primarily may involve data storage, both when and where, if used. As with intelligence, it may be that either some or no storage or memory may be made available in/by the electronics 103 on-board device 100. If some storage, whether a little or a lot, is made available on device 100, then, flow path 312*a* to and through path 312*c* may be used to achieve some storing of data 305. This may in many cases then, though not necessarily be before transmission or analysis (note, for some types of data multiple paths may be taken simultaneously, in parallel though perhaps not at the same time or serially (eg., paths 312*b* and 312*c* need not be taken totally to the exclusion of the other), so that storage and transmission or storage and analysis may occur without necessarily requiring a completion of any particular operation before beginning or otherwise implementing another). Thus, after (or during) storage 305, flow path 315*a* may be followed for stored data which may then be transmitted, by path 315*b* to operation 303, and/or analyzed, by path 315*c* to operation 304. In such a storage example, which in many cases may also be an on-board storage example, data can be collected then stored in local memory and later off-loaded/transmitted to one or more robust computing resources (e.g., FIG. 4) for analysis. Frequently, this can include long term data collection, e.g., in the manner of days or weeks or even longer, and may thus include remote collection when a patient is away from a doctor's office or other medical facilities. Thus, data can be collected from the patient in the patient's real world circumstances. Then, after collection, the data can be transmitted from its storage on device 100 back to the desired computing resource (FIG. 4, e.g.), and such transmission might be wireless or wired or come combination of both, as for example a blue tooth or WiFi connection to a personal computer (FIG. 4 for one example) which might then communicate the data over the internet to the designated computer for final analysis. Another example might include a USB connection to a computer, either to a PC or a mainframe (FIG. 4), and may be to the patient computer or to the doctor computer for analysis.

If little or no storage or memory is resident on device 100 (or in some examples even where there may be a large amount of resident memory available), then, relatively soon after collection, the data would need to or otherwise might desirably either or both be transmitted and then stored, see path 313*a* after operation 303, and/or transmitted and analyzed, paths 312 and 313. If path 313*a* is used, then, more typically, the data storage may be in/on computing resources (not shown in FIG. 3, but see FIG. 4 described below) off-board (though on-board memory could be used as well), and then, any of paths 315*a*, 315*b* and 315*c* may be used.

A feature hereof may include an overall system including one or more devices 100 and computing resources (see FIG. 4, for example) whether on-board device(s) 100, or separate, as for example in personal or mobile or hand-held computing devices (generally by FIG. 4), the overall system then providing the ability for the physician or doctor to have immediate, in-office analysis and presentation of collected test data. This would in some implementations allow for on-site data analysis from the device without utilization of a third party for data extraction and analysis.

Alternative implementations hereof may thus include one or more hardware and software combinations for multiple alternative data source interpretations. As noted above, a device 100 hereof includes hardware that monitors one or more of various physiologic parameters, then generates and stores the associated data representative of the monitored parameters. Then, a system which includes hardware such as device 100 and/or the parts thereof, and software and computing resources (FIG. 4, generally) for the processing thereof. The system then includes not only the collection of data but also interpretation and correlation of the data.

For example, an electrocardiogram trace that reveals a ventricular arrhythmia during intense exercise may be interpreted differently than the same arrhythmia during a period of rest. Blood oxygen saturation levels that vary greatly with movement can indicate conditions that may be more serious than when at rest, inter alia. Many more combinations of the four physiologic parameters are possible, and the ability of software hereof to display and highlight possible problems will greatly aid the physician in diagnosis. Thus, a system as described hereof can provide beneficial data interpretation.

Figure 4:
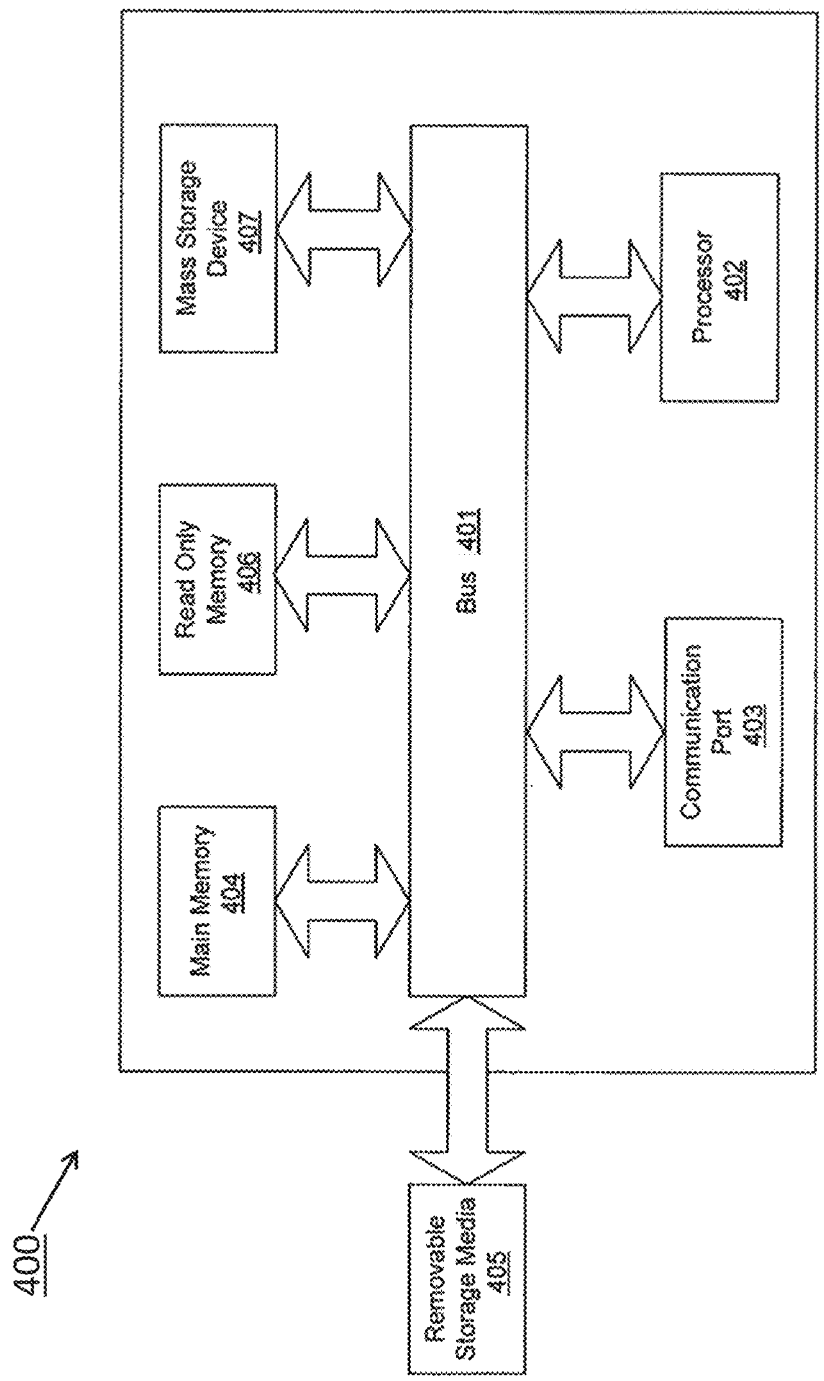
FIG. 4 illustrates an exemplary computer system or computing resources with which implementations hereof may be utilized.

Some of the features which can assist toward this end may be subsumed within one or more of operations 303 and 304 of FIG. 3, wherein data collected on a device 100 can rather simply be communicated/transmitted to computing resources (again, whether on-board device 100 or discrete therefrom as e.g., FIG. 4). For an example, when a patient having had a device applied (operation 301) may return to a physician's office after a test period wherein data was collected (operation 302) the device is connected via one or more data transmission alternatives, as for example, USB to a computer (Windows or Mac) (generally with reference to FIG. 4 and description thereof) in the office, allowing immediate analysis by the physician while the patient waits (note, the device 100 may first have been removed from the patient or might remain thereon pending transmission and analysis for determination of whether more data may be desired). In some implementations, data analysis time may be relatively quick, at approximately 15 minutes in some implementations, and might be achieved with a user-friendly GUI (Graphic User Interface) to guide the physician through the analysis software.

The analysis/software package may be disposed to present the physician with results in a variety of formats. In some implementations, an overview of the test results may be presented, either together with or in lieu of more detailed results. In either case, a summary of detected anomalies and/or patient-triggered events may be provided, either as part of an overview and/or as part of the more detailed presentation. Selecting individual anomalies or patient-triggered events may provide desirable flexibility to allow a physician to view additional detail, including raw data from the ECG and/or from other sensors. The package may also allow data to be printed and saved with annotations in industry-standard EHR formats.

In one implementation, patient data may be analyzed with software having the one or more of the following specifications. Some alternative capabilities may include: 1. Data Acquisition; i.e., loading of data files from device; 2. Data Formatting; i.e., formatting raw data to industry standard file formats (whether, e.g., aECG (xml); DICOM; or SCP-ECG) (note, such data formatting may be a part of Acquisition, Storage or Analysis, or may have translation from one to another (e.g., data might be better stored in a compact format that may need translation or other un-packing to analyze)); 3. Data Storage (whether local, at a clinic/medical facility level or e.g., in the Cloud (optional and allows offline portable browser based presentation/analysis); 4. Analysis which inter alia, may include, e.g., noise filtering (High pass/Low pass digital filtering); and/or QRS (Beat) detection (in some cases, may include Continuous Wave Transform (CWT) for speed and accuracy); and/or 5. Data/Results Presentation, whether including one or more graphical user interface(s) (GUIs) perhaps more particularly with an overall Summary and/or General Statistics and/or Anomaly Summary of Patient triggered event(s); presentation of additional levels of detail whether of Strip view(s) of anomaly data by incident (previous, next) Blood Oxygen saturation, stress correlation or the like; and/or allowing care provider bookmarking/annotations/notes by incident and/or Print capability.

Further, on alternative combinations of hardware with proprietary software packages: I) One on-device software package may be adapted to store the measurements from the data signals acquired from one or more of EKG/ECG (whether right leg and/or p-, qrs- and/or t-waves), or O2 saturation, or xyz acceleration, in a time concordant manner, so that a physician may access a temporal history of the measurements (say, in some examples, over a 1-2 week interval), which would provide useful information on what the patient's activity level was prior to, during, and after the occurrence of a cardiac event. ii) an alternative to alternately manage the real-time transmission of the real-time measured parameters to a nearby station or relay. And/or; iii) an off-device ECG analysis software aimed at recognizing arrhythmias.

The software mentioned above may be industry understood software provided by a 3rd party, or specially adapted for the data developed and transmitted by and/or received from a wearable device 100 hereof. Thorough testing using standard (MIT-BIH/AHA/NST) arrhythmia databases, FDA 510(k) approvals preferred. Such software may be adapted to allow one or more of automated ECG analysis and interpretation by providing callable functions for ECG signal processing, QRS detection and measurement, QRS feature extraction, classification of normal and ventricular ectopic beats, heart rate measurement, measurement of PR and QT intervals, and rhythm interpretation.

In many implementations, the software may be adapted to provide and/or may be made capable of supplying one or more of the following measurements:

1. Heart Rate Min, Max and Average
2. QRS duration average
3. PR interval average
4. QT interval average
5. ST deviation average and, may be adapted to recognize a broad range of arrhythmias such as those set forth here:

1. SINUS RHYTHM
2. SINUS RHYTHM+IVCD
3. SINUS BRADYCARDIA
4. SINUS BRADYCARDIA+IVCD
5. SINUS TACHYCARDIA
6. PAUSE
7. UNCLASSIFIED RHYTHM
8. ARTIFACT

This first group of 8 given above are arrhythmia types that may be recognizable even if there is no discernible P wave. They are the ones typically recognized by existing products in the outpatient monitoring market that we propose to address.

A second set or group of arrhythmias; below, may require a discernible and measurable P wave. Some implementations hereof may be adapted to be able to detect and recognize them, as device 100 may be able as described above to detect P waves, depending of course, and for example, on whether the strength of the P wave is affected by device 100 placement or patient physiology.

Figure 5A:
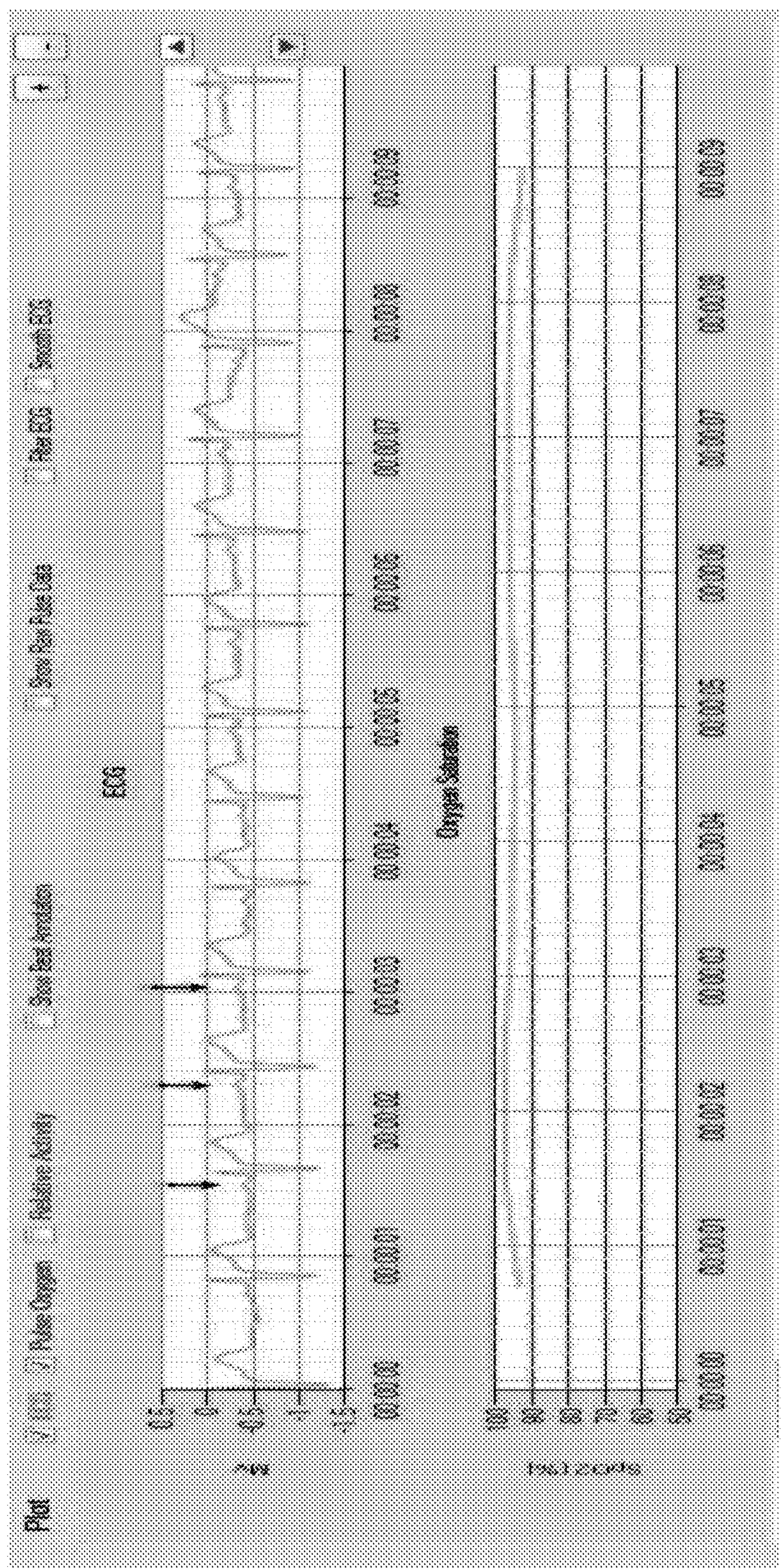
FIG. 5, which includes sub-part FIGS. 5A-5D, provides alternative screenshots of alternative software implementations according hereto.

9. ATRIAL FIBRILLATION/FLUTTER SVR (slow)
10. ATRIAL FIBRILLATION/FLUTTER CVR (normal rate)
11. ATRIAL FIBRILLATION/FLUTTER RVR (rapid
12. FIRST DEGREE AV BLOCK+SINUS RHYTHM
13. FIRST DEGREE AV BLOCK+SINUS TACHYCARDIA
14. FIRST DEGREE AV BLOCK+SINUS BRADYCARDIA
15. SECOND DEGREE AV BLOCK
16. THIRD DEGREE AV BLOCK
17. PREMATURE ATRIAL CONTRACTION
18. SUPRAVENTRICULAR TACHYCARDIA
19. PREMATURE VENTRICULAR CONTRACTION
20. VENTRICULAR COUPLET
21. VENTRICULAR BIGEMINY
22. VENTRICULAR TRIGEMINY
23. IDIOVENTRICULAR RHYTHM
24. VENTRICULAR TACHYCARDIA
25. SLOW VENTRICULAR TACHYCARDIA Further in alternative software implementations; some sample screenshots are shown in FIG. 5. A first such alternative is shown in FIG. 5A, which is an example screenshot showing ECG and Oxygen Saturation data taken by using a patch device such as a device 100 hereof. An extremely clean signal is shown (no filtering or smoothing has been done on this data). Distinct p-waves are also shown (3 of which are shown as an example with arrows). P wave detection can be extremely important for ECG anomaly detection. Oxygen Saturation, as measured by Pulse Oxymetry, is shown on the bottom plot. This is data taken by the a device on the chest, and is taken in time concordance with the ECG data.

Figure 5B:
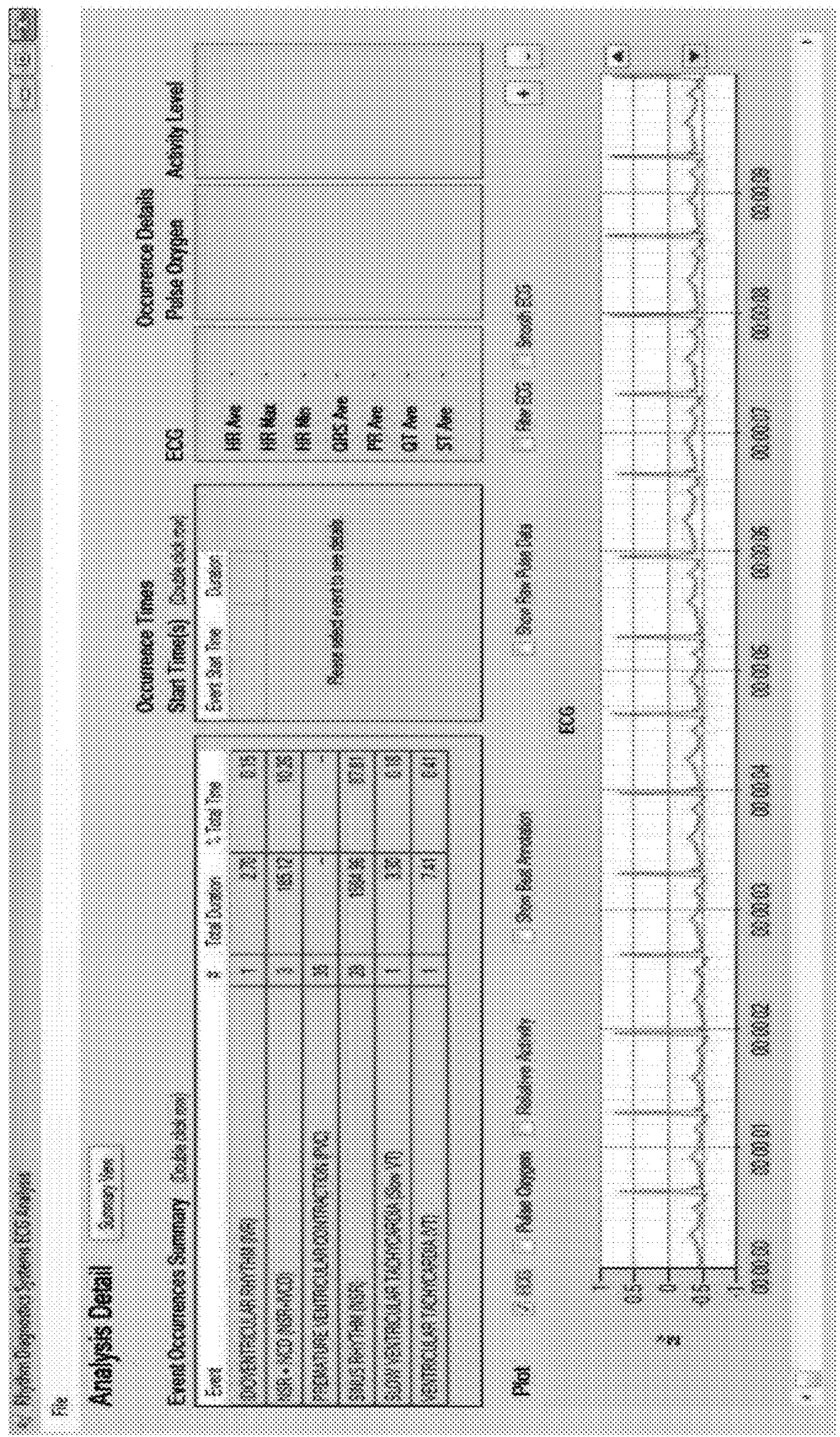

Another alternative is shown in FIG. 5B, which is an example screenshot of Analysis Software. This is a sample of ECG data taken from the MIT-BIH Arrhythmia Database, Record 205. As analyzed by the Analysis system hereof, we see in the Event Occurrences Summary list (top, left) five (5) anomaly types (plus normal sinus rhythm). This list also shows the number of occurrences of each anomaly, total duration of the anomaly in the complete ECG, and the percent time this anomaly occurs in the complete ECG. To view specific instances of each anomaly, the user double clicks the specific row in the Event Occurrences Summary list, as shown in FIG. 5C.

Figure 5C:
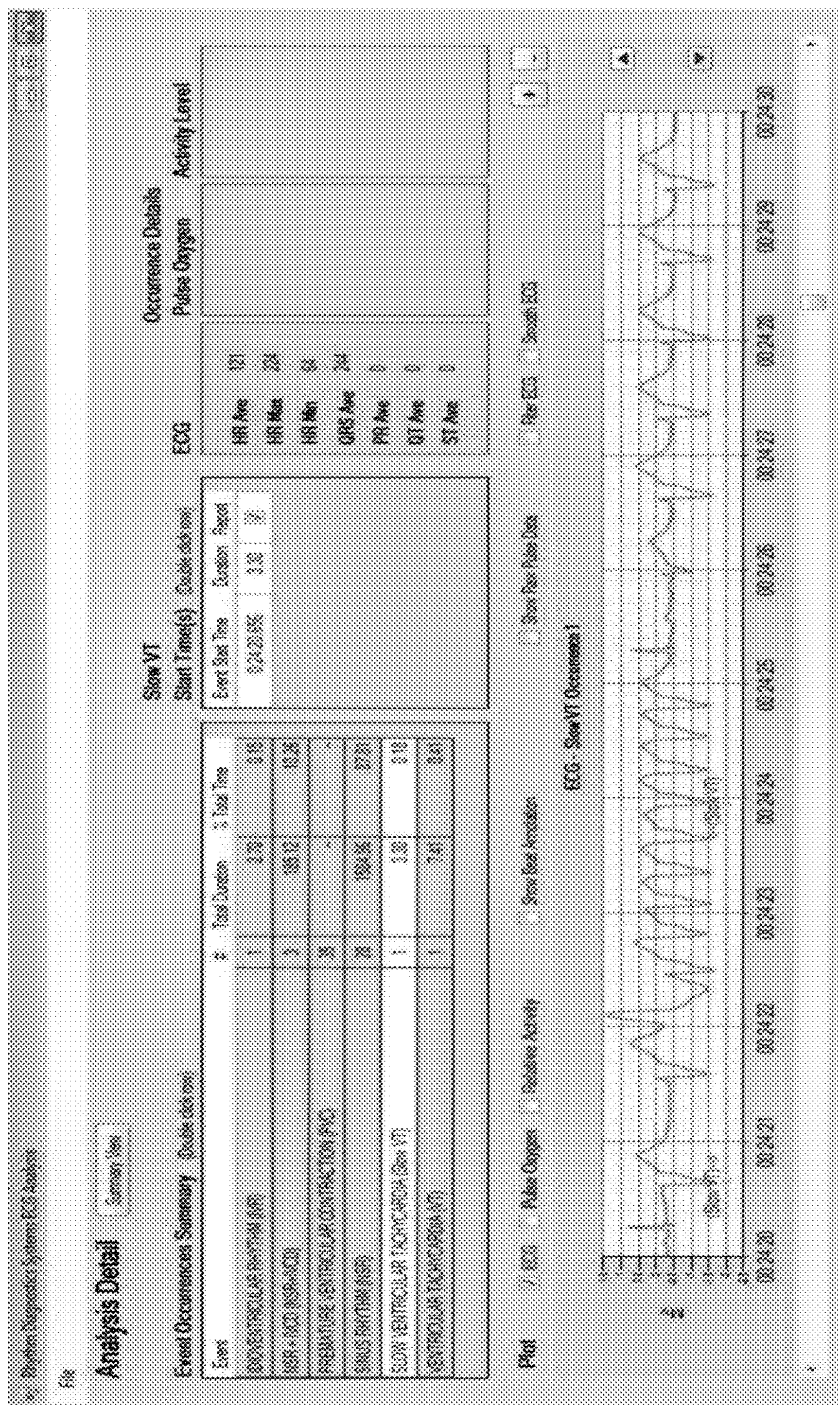

As introduced, FIG. 5C is an example screenshot showing specific instance of Ventricular Tachycardia. The ECG plot automatically navigates to the specific time in the ECG waveform, and marks the beginning and end of the event. More detailed data about this specific event is now shown in the Occurrence Details: HR Average, HR Max, etc. for the duration of this event. To show the instances of another anomaly in this ECT, the user can click on the Premature Ventricular Contraction (PVC) row of the Event Occurrences Summary, as shown FIG. 5D.

Figure 5D:
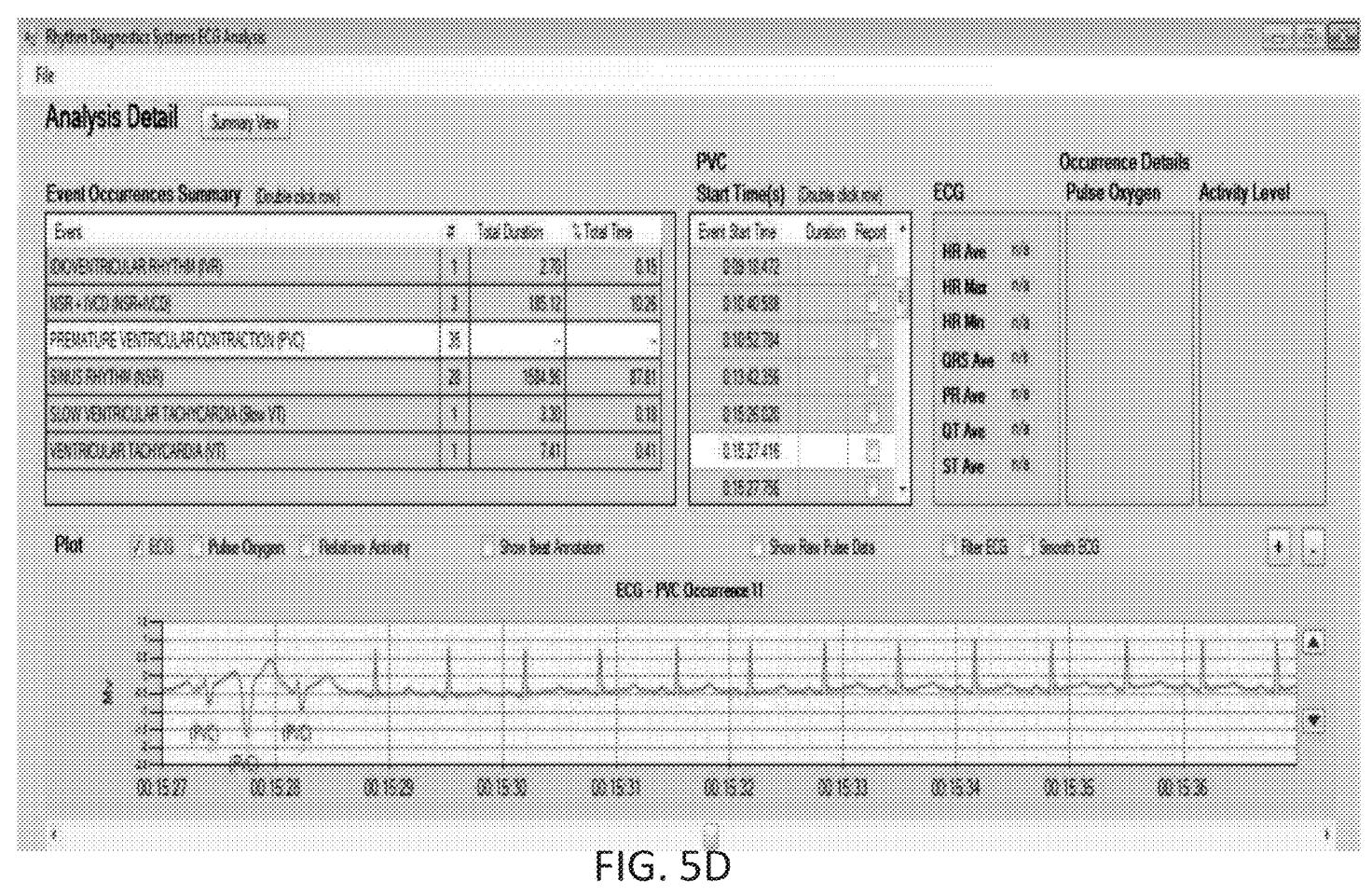

As introduced, FIG. 5D is an example screenshot showing specific instance of Premature Ventricular Contraction. This shows occurrences of the PVC. The Start Times list (middle top) shows all instances of PVC occurrences in this ECG, and lists the start time for each occurrence. In this case, the user can click on the PVC that starts at 00:15:27 (the $11^{th}$ occurrence). The ECG plot is automatically taken to this point in time to show and indicate the PVC instances in the waveform. Since there are 3 instances of a PVC in this timeslot, all 3 occurrences are marked.

Some further alternatives may include data transmission and/or interpretation by local medical facilities, whether physician or doctor offices or e.g., ICU/CCU (Intensive Care/Coronary Care Units). Accordingly, a device 100 hereof that will measure one or more of a variety of physiologic signals, possibly including electrocardiogram, photoplethysmogram, pulse oximetry and/or patient acceleration signals will be placed on the patient's chest and held with an adhesive as described herein. The device transmits the physiologic signals wirelessly or by wire (e.g., USB) to a nearby base station for interpretation and further transmission, if desired. The wireless transmission may use Bluetooth, WiFi, Infrared, RFID (Radio Frequency IDentification) or another wireless protocol. The device may be powered by wireless induction, battery, or a combination of the two. The device 100 monitors physiological signals and/or collects data representative thereof. The collected data may then be transmitted wirelessly or by wire connection, in real time, to the nearby base station. The device may be wirelessly powered by the base station or by battery, removing the need for wires between the patient and the station.

Thus, some of the alternative combinations hereof may include one or more of: 1) medical grade adhesives (from many possible sources) selected for their ability to maintain in intimate contact with the skin without damaging it, for several days (up to, say 10 days or two weeks in some examples), as well as operability with different types of sensors; 2) conductive electrodes or photo-sensitive detectors able to supply electrical signals from the skin or from the photo-response of cutaneous or subcutaneous tissues to photo-excitation; 3) amplifiers, microprocessors and memories, capable of treating these signals and storing them; 4) power supply for the electronics hereof with stored or with wirelessly accessible re-chargeability; 5) flex circuits capable of tying the above elements together within a flexible strip capable of conforming to a cutaneous region of interest.

Examples of physiological parameters that may be subject to monitoring, recordation/collection and/or analyzing may include one or more of: electrocardiograms, photo responses of photo-excited tissues for e.g., oxygen saturation of blood; pulse rates and associated fluctuations; indications of physical activity/acceleration. One or more of these may be used in monitoring ambulatory cardiac outpatients over several days and nights, which could thereby provide for recording, for post-test analysis, several days' worth of continuous ECG signals together with simultaneous recording of O2 saturation and an index of physical exertion. Similarly, one or more of these may be used in monitoring ambulatory pulmonary outpatients over several days and nights for recording, for post-test analysis, O2 saturation together with simultaneous recording of an index of physical activity. Alternatively and/or additionally, one or more of these could be used for monitoring in-patients or other patients of interest, as for example neonatals, wirelessly (or in some cases wired), whether in clinics, emergency rooms, or ICUs, in some instances detecting the parameters of EKG, O2 and/or physical exertion, but instead of storing them would transmit them wirelessly to either a bedside monitor or a central station monitor, thus freeing the patient from attachment to physical wires.

An exemplary computer system or computing resources which may be used herewith will now be described, though it should be noted that many alternatives in computing systems and resources may be available and operable within the reasonably foreseeable scope hereof so that the following is intended in no way to be limiting of the myriad possible computational alternatives properly intended within both the spirit and scope hereof.

Some of the implementations of the present invention include various steps. A variety of these steps may be performed by hardware components or may be embodied in machine-executable instructions, which may be used to cause a general-purpose or special-purpose processor programmed with the instructions to perform the steps. Alternatively, the steps may be performed by a combination of hardware, software, and/or firmware. As such, FIG. 4 is an example of computing resources or a computer system 400 with which implementations hereof may be utilized. According to the present example, a sample such computer system 400 may include a bus 401, at least one processor 402, at least one communication port 403, a main memory 404, a removable storage media 405, a read only memory 406, and a mass storage 407. More or fewer of these elements may be used in a particular implementation hereof.

Processor(s) 402 can be any known processor, such as, but not limited to, an Intel® Itanium® or Itanium 2® processor(s), or AMD® Opteron® or Athlon MP® processor(s), or Motorola® lines of processors. Communication port(s) 403 can be any of an RS-232 port for use with a modem based dialup connection, a 10/100 Ethernet port, a Universal Serial Bus (USB) port, or a Gigabit port using copper or fiber. Communication port(s) 403 may be chosen depending on a network such a Local Area Network (LAN), Wide Area Network (WAN), or any network to which the computer system 400 connects or may be adapted to connect.

Main memory 404 can be Random Access Memory (RAM), or any other dynamic storage device(s) commonly known in the art. Read only memory 406 can be any static storage device(s) such as Programmable Read Only Memory (PROM) chips for storing static information such as instructions for processor 402.

Mass storage 407 can be used to store information and instructions. For example, hard disks such as the Adaptec® family of SCSI drives, an optical disc, an array of disks such as RAID, such as the Adaptec family of RAID drives, or any other mass storage devices may be used.

Bus 401 communicatively couples processor(s) 402 with the other memory, storage and communication blocks. Bus 401 can be a PCI/PCI-X or SCSI based system bus depending on the storage devices used.

Removable storage media 405 can be any kind of external hard-drives, floppy drives, IOMEGA® Zip Drives, Compact Disc-Read Only Memory (CD-ROM), Compact Disc-Re-Writable (CD-RW), Digital Video Dis-Read Only Memory (DVD-ROM).

The components described above are meant to exemplify some types of possibilities. In no way should the aforementioned examples limit the scope of the invention, as they are only exemplary embodiments.

Embodiments of the present invention relate to devices, systems, methods, media, and arrangements for monitoring and processing cardiac parameters and data, inter alia. While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

What is claimed is:

1. A method for reducing noise in cardiac monitoring using a wearable monitoring device having at least two electrodes for cardiac monitoring; the method comprising:

applying the wearable monitoring device externally to a subject, the subject having at least a right leg;

operating circuitry adaptations comprising:

operating a first electrode;

operating a second electrode also referred to as a proxy driven-right-leg electrode mimicking a right leg electrode; the second electrode being the proxy driven-right-leg electrode affixed on the subject other than on the right leg of the subject;

operating a voltage or current driver operatively connected to the first and second electrodes to drive one or both a voltage or current to the second electrode;

operating a reference voltage configured to be operatively associated with the first and second electrodes;

driving by application of a voltage or current, to the second electrode also known as the proxy driven-right-leg electrode, maintaining the voltage of the first electrode at a relationship, other than a common mode voltage of multiple additional electrodes, to the voltage of an additional electrode;

generating an output representative of a noise-reduced physiological signal for cardiac monitoring.

2. A method according to claim 1 further comprising one or both:

transmitting the data from the wearable device;

or, transmitting the data from the wearable device; and, storing the data prior to one or both of transmitting or analyzing the data.

3. A circuit for mimicking a right leg electrode using a reference electrode as proxy therefor; the circuit comprising the combination A), B), C), D) with one or more of W), X), Y), Z):

A) a connection to a first electrocardiogram electrode;

B) a connection to a second electrocardiogram electrode;

C) a connection to a reference electrocardiogram electrode; and,

D) an amplifier; the electrode connections all connected to the amplifier; the amplifier maintaining the voltage of the first electrode at a relationship, other than a common mode voltage of multiple additional electrodes, to the voltage of an additional electrode, a proxy driven right leg signal being measurable using a reference electrode and being used in generating an output representative of a noise-reduced physiological signal for cardiac monitoring; the reference electrode being the proxy driven-right-leg electrode affixed on a subject other than on a right leg of the subject;

and

W) a connection to a sense electrode;

X) a connection to a drive electrode;

Y) a bias voltage input; and,

Z) an amplifier; the electrode connections and bias voltage input connected to the amplifier; the amplifier output connected to the drive electrode, an inverting input to the sense electrode, and a non-inverting input to a bias voltage; the amplifier maintaining the voltage of the first electrode at a relationship, other than the common mode voltage of multiple additional electrodes, to the voltage of an additional electrode; the proxy driven right leg signal being measurable using a third electrode and being used in generating an output representative of a noise-reduced physiological signal for cardiac monitoring; the third electrode being the proxy driven-right-leg electrode affixed externally on a subject other than on a right leg of the subject.

4. A method according to claim 1 further comprising:

collecting data representative of physiological signals; and, analyzing the data.

5. A method according to claim 1 the maintaining operation further comprising one or more of:

maintaining the voltage of the first electrode at a relationship equal to or approximately equal to the bias or reference or ground voltage;

maintaining the voltage of the first electrode at a relationship of one or more of a weighted sum, average, or common-mode voltage of the first electrode and at least one additional voltage; and, maintaining the voltage of the first electrode at a relationship; of one or more of a weighted sum, average, or common-mode voltage of the first electrode and one or more of a number of additional electrodes equal to or approximately equal to the bias voltage and one or more of a number of additional electrodes equal to or approximately equal to the bias voltage.

6. A method according to claim 1 wherein the at least one additional electrode includes one or more of a number of additional electrodes.

7. A method according to claim 1 wherein the physiological signal includes one or both an ECG or a photoplethysmography (PPG) signal.

* * * * *